(12) United States Patent
Bernard et al.

(10) Patent No.: US 8,372,590 B2
(45) Date of Patent: Feb. 12, 2013

(54) ISOLATION AND ENUMERATION OF CELLS FROM A COMPLEX SAMPLE MATRIX

(75) Inventors: Bruce J-C Bernard, Austin, TX (US); John C. Carrano, Austin, TX (US); Amy L. Altman, Round Rock, TX (US)

(73) Assignee: Luminex Corporation, Austin, TX (US)

( * ) Notice: Subject to any disclaimer, the term of this patent is extended or adjusted under 35 U.S.C. 154(b) by 810 days.

(21) Appl. No.: 12/349,833

(22) Filed: Jan. 7, 2009

(65) Prior Publication Data

US 2009/0246796 A1     Oct. 1, 2009

Related U.S. Application Data

(60) Provisional application No. 61/019,485, filed on Jan. 7, 2008.

(51) Int. Cl.
*G01N 33/543* (2006.01)
(52) U.S. Cl. .......................................................... 435/7.1
(58) Field of Classification Search .................. None
See application file for complete search history.

(56) References Cited

U.S. PATENT DOCUMENTS

| | | | |
|---|---|---|---|
| 4,230,685 A | 10/1980 | Senyei et al. | 436/526 |
| 5,736,330 A | 4/1998 | Fulton | 435/6 |
| 5,981,180 A | 11/1999 | Chandler et al. | 435/6 |
| 5,993,665 A | 11/1999 | Terstappen et al. | 210/695 |
| 6,057,107 A | 5/2000 | Fulton | 435/6 |
| 6,265,229 B1 | 7/2001 | Fodstad et al. | 436/526 |
| 6,268,222 B1 | 7/2001 | Chandler et al. | 436/523 |
| 6,449,562 B1 | 9/2002 | Chandler et al. | 702/19 |
| 6,514,295 B1 | 2/2003 | Chandler et al. | 8/607 |
| 6,524,793 B1 | 2/2003 | Chandler et al. | 435/6 |
| 6,528,165 B2 | 3/2003 | Chandler | 428/402.2 |
| 6,773,812 B2 | 8/2004 | Chandler et al. | 428/403 |
| 2002/0172987 A1* | 11/2002 | Terstappen et al. | 435/7.23 |
| 2006/0024756 A1 | 2/2006 | Tibbe et al. | 435/7.2 |
| 2006/0159962 A1 | 7/2006 | Chandler et al. | 428/403 |
| 2006/0216696 A1 | 9/2006 | Goguen | 435/7.32 |
| 2007/0064990 A1 | 3/2007 | Roth | 382/128 |
| 2007/0281311 A1 | 12/2007 | Roth et al. | 435/6 |

FOREIGN PATENT DOCUMENTS

| | | |
|---|---|---|
| WO | WO 03069421 A2 * | 8/2003 |
| WO | WO 2006/041453 | 4/2006 |
| WO | WO 2007/133465 | 11/2007 |
| WO | WO 2007/143615 | 12/2007 |

OTHER PUBLICATIONS

International Search Report and Written Opinion, issued in International Application No. PCT/US2009/030274, mailed Jun. 18, 2009.
Dynal, "Cell separation and protein purification," *Dynal Technical Handbook*, 2nd Edition, 1996, table of contents only.
Olsvik et al., "Magnetic separation techniques in diagnostic microbiology," *Clinical Microbiology Reviews*, 7(1):43-54, 1994.

* cited by examiner

*Primary Examiner* — Brian J Gangle
(74) *Attorney, Agent, or Firm* — Fulbright & Jaworski L.L.P.

(57) ABSTRACT

The present invention relates to methods and systems for labeling, isolating, detecting and enumerating biological cells, or other biological analytes of interest present in a sample, where the capturing complex may also serve as a labeling agent. In one embodiment, the capture complex is an encoded magnetic bead coupled to antibodies having a specific affinity for a cell surface protein on a cell of interest. The methods and systems of the present invention can be used for quantitative or qualitative detection.

36 Claims, 12 Drawing Sheets

ISOLATION AND ENUMERATION OF CELLS FROM A COMPLEX SAMPLE MATRIX

This application claims priority to U.S. Provisional Patent Application Ser. No. 61/019,485, filed on Jan. 7, 2008. The entirety of the above-referenced disclosure is incorporated by reference.

BACKGROUND OF THE INVENTION

A. Field of the Invention

The present invention relates generally to the isolation and detection of biological analytes such as cells, spores, or bacteria. More particularly, the present invention relates to the immunomagnetic separation of biological agents from complex samples.

B. Description of Related Art

The study, characterization and census of biological cells has always depended on the use of imaging tools that allow for the visualization of what the naked eye could not see directly. Since the first scientific observation of cells reported in 1665 by Robert Hooke (The Cell—A molecular approach; Geoffrey M. Cooper. ASM Press. 1997), the field of microscopy has enabled the field of cell biology. From the basic early bright field light microscopes to the most recent scanning electron microscopes, cell biologists exploited the increasing magnifications and resolution capabilities of these technologies. Today, the integration of digital imaging with these powerful microscopes has expanded the scope of this field even more. Microscopy can now be combined with powerful image processing techniques enabling for the rapid and automated analysis of a wide variety of samples.

While the imaging capabilities of microscopes have evolved significantly over centuries, sample preparation is usually still a discrete task performed prior to imaging. Usually a targeted element of interest in the sample (the nucleus of a cell, or the membrane of a cell, etc.) is stained or dyed in order to enable its visualization. There is no integrated apparatus that performs all needed steps of an analysis such as the preparation of a sample, the imaging and characterization of a target cell, and regeneration of the imaging chamber after analysis of the sample. Microscope glass slides and cover slips are still widely used to accommodate samples due to their simplicity of use and low cost. Many lab-on-a-chip techniques use some form of microscopy (bright field or fluorescent microscopy) and imaging approach as a detector; however, there is often a lack of integration around the compact imaging chamber. In this respect, many lab-on-a-chip devices are still in their infancy. Scanning electron microscope (SEM) techniques also lack sample preparation automation, and each sample is required to be individually mounted on a pin and coated with a metal prior to analysis. Therefore the main drawback of microscopy is throughput. Sample preparation, positioning of the sample onto the focal plan and localization of the area of interest remain laborious processes.

The characterization of cells (size, shape) and most specifically the characterization of markers on the surface of the cells can also be done by flow cytometry. This technique was a great improvement as far as throughput was concerned. Since the late 1970s, flow cytometry has enabled scientists to analyze a variety of cell types and offers numerous advantages over other cell-based techniques including: speed, preservation of cell viability and cellular functions, and simultaneous measurements of multiple cellular parameters.

The appeal of flow cytometry arises from the flexibility and sensitivity of fluorescence technology combined with the technique's high speed and powerful data integration capabilities. Flow cytometry currently is the most commonly used method and the gold standard for cell sorting and analysis (Bioinformatics Market Research 2006 Report #06-030: "influencing brand preference in the flow cytometry market"). While Flow cytometers brought a lot of capability to cell analysis, they are expensive and technically challenging to operate. Even the most affordable flow cytometer models are priced over $100,000, and more sophisticated models are priced at over $300,000. In addition, flow cytometers require well-trained operators and are very sensitive to shifts in their optical alignment. Consequently the overall purchasing and operating costs of these instruments make them inaccessible to many laboratories, particularly those located in resource-poor countries.

SUMMARY OF THE INVENTION

In one embodiment, the present invention provides a method for immobilizing and detecting a biological analyte in a sample comprising: (a) obtaining a first capture complex comprising an encoded magnetic particle coupled to a capture agent having a specific affinity for a particular epitope on a first biological analyte that may be present in the sample; (b) contacting the sample with the capture complex; (c) introducing an aliquot of the sample into a chamber; (d) applying a magnetic field to the chamber to attract the capture complex to a surface of the chamber; and (e) detecting the biological analytes that are immobilized on the surface of the chamber by binding the capture complex.

In another embodiment, the present invention provides a method for immobilizing and detecting one or more biological analyte populations in a sample comprising: (a) obtaining a first capture complex comprising a first encoded magnetic particle and a first capture agent having a specific affinity for a particular epitope on a first biological analyte population that may be present in the sample; (b) obtaining a second capture complex comprising a second encoded magnetic particle and a second capture agent having a specific affinity for a particular epitope on a second biological analyte population that may be present in the sample; (c) contacting the sample with the first capture complex and the second capture complex; (d) introducing an aliquot of the sample into a chamber; (e) applying a magnetic field to the chamber to attract the first capture complex and the second capture complex to a surface of the chamber; and (f) detecting the first population of biological analytes that are immobilized on the surface of the chamber by binding the first capture complex and the second population of biological that are immobilized on the surface of the chamber by binding the second capture complex.

In one embodiment, the present invention provides a method for immobilizing and detecting a cell in a sample comprising: (a) obtaining a first capture complex comprising an encoded magnetic bead coupled to antibodies having a specific affinity for a particular epitope on a first cell that may be present in the sample; (b) contacting the sample with the capture complex; (c) introducing an aliquot of the sample into a chamber; (d) applying a magnetic field to the chamber to attract the capture complex to a surface of the chamber; and (e) detecting the cells that are immobilized on the surface of the chamber by binding the capture complex.

In another embodiment, the present invention provides a method for immobilizing and detecting one or more cell populations in a sample comprising: (a) obtaining a first capture complex comprising a first encoded magnetic bead and a first antibody having a specific affinity for a particular epitope on a first cell population that may be present in the sample; (b)

obtaining a second capture complex comprising a second encoded magnetic bead and a second antibody having a specific affinity for a particular epitope on a second cell population that may be present in the sample; (c) contacting the sample with the first capture complex and the second capture complex; (d) introducing an aliquot of the sample into a chamber; (e) applying a magnetic field to the chamber to attract the first capture complex and the second capture complex to a surface of the chamber; and (f) detecting the first population of cells that are immobilized on the surface of the chamber by binding the first capture complex and the second population of cells that are immobilized on the surface of the chamber by binding the second capture complex.

The sample may be contacted with a capture complex prior to introducing the sample into the chamber or after introducing the sample into the chamber. In certain aspects of the invention, the sample maybe contacted with additional different capture complexes, such as a second, third, fourth, fifth, sixth, seventh, eighth, ninth, tenth, twentieth, fiftieth or more capture complex. Each of the different capture complexes has a specific affinity for a different epitope and is uniquely encoded (e.g., spectrally distinct).

In certain embodiments, the methods further comprise enumerating the biological analytes (e.g., cells) that are immobilized on the surface of the chamber. The methods may further comprise determining whether a statistically significant number of the biological analytes are immobilized on the surface of the chamber, and introducing one or more additional aliquots of the sample into the chamber until a statistically significant number of the biological analytes are immobilized on the surface of the chamber. In certain aspects, the methods further comprise correlating the number of biological analytes detected with the number of biological analytes in the sample. The correlating may comprise, for example, determining a concentration of the biological analytes in the sample and/or determining the total number of biological analytes in the sample. Where two or more different biological analytes are assayed, the methods may comprise determining a ratio of the first population of biological analytes to a second population of biological analytes. The method may further comprise determining numbers, concentrations, and/or ratios of a second, third, fourth, fifth, sixth, seventh, eighth, ninth, tenth, or more populations of biological analytes.

In certain aspects of the invention, the encoded magnetic particles are paramagnetic or superparamagnetic. In some aspects, the encoded magnetic particles are encoded magnetic beads. The beads may be encoded, for example, with one or more fluorescent dyes. In some embodiments, the beads are about the size of the cells that they are to bind. In certain embodiments, the beads are between 5-8 µm, 6-8 µm, or 6-7 µm in diameter. In one embodiment, the beads are about 6.7 µm in diameter.

In some embodiments, the methods further comprising performing a washing step prior to the detection and enumeration of the biological analytes in the imaging chamber in order to remove components of a sample that have not been immobilized by the magnetic field. The washing step may be performed prior to each detection and enumeration in the sample loading process or it may be performed only prior to the final detection and enumeration step.

The biological analyte may be any biological target of interest. In particular embodiments the biological target is a cell. The cell may be, for example, a eukaryotic cell or a prokaryotic cell. Eukaryotic cells include, but are not limited to, mammalian cells, fish cells, amphibian cells, avian cells, reptilian cells, insect cells, plant cells, or fungus cells. In certain aspects of the invention, the cells are lymphocytes, leukocytes or monocytes. The prokaryotic cells may be, for example, bacteria cells or bacterial spores. Where the biological target is a cell, the epitopes detected by the capture agents and labeling agents are preferably epitopes on the surface of the cell. For example, if the biological target is a T cell, the epitopes may be one or more of CD3, CD4, and/or CD8.

The biological target may be in a sample. A sample may be any composition containing a cell or suspected of containing a cell. In certain aspects of the invention, the sample may be a bodily fluid (including but not limited to whole blood, serum, saliva, urine, sperm). In other aspects of the invention, the sample is an environmental sample such as a soil, water, or air sample, or other substance found in one's surroundings.

The methods and systems of the present invention may be used in a wide variety of applications including, but not limited to, detecting and identifying bacteria in bacterial sepsis in patients; immunophenotyping of leukemia/lymphoma by identifying antigenic determinants on the cell surface of B cells and T cells; monitoring immunologic response to organ transplantation by detecting changes in cellular components of the immune system; detecting and enumerating CD34+ cells, which provides a measure of the adequacy of immune suppression through T cell receptors analysis; platelet detection and enumeration using, for example, CD42a as a marker; PNH (paroxysmal nocturnal hemoglobinuria) diagnosis by determining the presence or absence of GPI-anchored proteins (CD59, CD55), which are missing on the surface of PNH blood cells. The methods and systems described herein provide several advantages in the analysis of complex samples such as blood. For example, depletion of red blood cells from a blood sample by lysis or centrifugation is unnecessary with the presently described methods and systems because red blood cells can simply be removed by the washing of non-magnetic materials from the imaging chamber. Additionally, depletion of undesired cells can be replaced by the identification of these cells by other bead sets, which is possible due to the multiplexing capability of the presently described methods and systems. Moreover, this multiplexing removes the need to use multiple stains to identify cells based on their color and morphology.

The capture agents may be antibodies, aptamers, nucleic acid probes such as but not limited to DNA or RNA, proteins, or any other molecule, natural or synthesized, that binds specifically to a biological analyte of interest. The capture complexes are magnetically responsive because they comprise magnetic particles. Multiple units of a capture complex may bind to a single biological analyte to create a magnetically responsive aggregate or cluster attractable by the magnetic field of the apparatus. Because the magnetic particles (e.g., beads) are themselves labeled (i.e., encoded), additional labeling agents are not needed to detect and identify the biological analytes bound to the capture complex. The detection process may include a classification step to characterize the Median Fluorescent Intensity (MFI) of the capture agents bound to a biological analyte. In certain embodiments of the invention, a cell of interest may be labeled with a generic reporter dye that would stain any cell's membrane (e.g. Gram stain) or cell's nuclei (e.g. DAPI) in order to differentiate a cluster of beads around a cell of interest from a nonspecific cluster of beads (no cells captured within the cluster). In such an embodiment, the detection process may include a classification step to characterize the Median Fluorescent Intensity (MFI) of the cluster and a reporter step to ensure that a cell is within the cluster.

In another embodiment, the present invention provides a method for detecting and identifying bacteria in a bacterial sepsis patient comprising: (a) obtaining a sample (e.g., a blood sample) from a patient suspected of having bacterial sepsis; (b) obtaining a plurality of different capture complexes, each of the different capture complexes comprising a uniquely encoded magnetic bead and an antibody having a specific affinity for a particular epitope on a bacteria that may be present in the sample; (c) contacting the sample with the plurality of capture complexes; (d) introducing an aliquot of the sample into a chamber; (e) applying a magnetic field to the chamber to attract the capture complexes to a surface of the chamber; and (f) detecting the bacteria that are immobilized on the surface of the chamber by binding the capture complexes. In certain embodiments, the method further comprises enumerating and identifying the bacteria. The identity of the bacteria may be determined by the uniquely encoded magnetic beads that are bound to bacteria. In one embodiment, the method for detecting and identifying bacteria in a bacterial sepsis patient further comprises obtaining a capture complex comprising a uniquely encoded magnetic bead and an antibody having a specific affinity for platelets and contacting the sample with this capture complex such that the platelets can be detected and identified. By detecting platelets in the sample, the extent of bacterial sepsis may be determined by comparing the number or concentration of bacteria in the sample to the number or concentration of platelets in the sample. In certain embodiments, the method may be used to immobilize, detect, and identify one or more of the following bacteria: *Escherichia coli, Listeria monocytogenes, Neisseria meningitides, Streptococcus pneumoniae, Staphylococcus aureas, Haemophilus influenzae, Pseudomonas aeruginosa,* and *Streptococcus pyogenes*. Although the above method is described in the context of bacterial sepsis, it may also be adapted for detecting and or identifying other bacterial infections (e.g., bacterial meningitis) by obtaining a sample from the relevant bodily fluid or tissue and contacting the sample with capture complexes with specific affinity for the bacteria suspected of being present in the sample.

The present invention also provides kits that provide various components that may be used in connection with the methods disclosed herein. In one embodiment, the kit may comprise one or more capture complexes. In certain aspects, the kit comprises one or more distinct populations of encoded magnetic beads coupled to antibodies having specific affinities for particular epitopes on biological analytes. In one embodiment, the present invention provides a kit for detecting bacterial sepsis in a patient, wherein the kit comprises capture complexes for one or more of the following bacteria: *Escherichia coli, Listeria monocytogenes, Neisseria meningitides, Streptococcus pneumoniae, Staphylococcus aureas, Haemophilus influenzae, Pseudomonas aeruginosa,* and *Streptococcus pyogenes*

In one embodiment, the present invention provides a system for performing immunogenic capture and imaging of biological targets. In certain aspects, the system comprises: an imaging system; encoded magnetic capture complexes adapted to be introduced into the imaging system, the capture complexes having specific affinity for particular epitopes on biological target(s); a magnet for selectively introducing a magnetic field to the imaging system for immobilizing the capture complexes and any biological targets bound thereto.

It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4A illustrates an imaging chamber field of view in which specific clusters (cell+beads) as well as non-specific bead clusters and single beads are present. The specific clusters are circled in FIG. 4A. FIG. 4B shows a classification map that may be generated using the median fluorescent intensity (MFI) of each cluster. Each region of the map is specific to a bead set and corresponds to a surface marker of the targeted cell.

DESCRIPTION OF ILLUSTRATIVE EMBODIMENTS

The present invention relates to methods and systems for labeling, isolating, detecting and enumerating biological cells, or other biological analytes of interest present in a sample, where the capturing agent may also serve as a labeling agent. The methods may be implemented on imaging systems such as those described herein and on the apparatus described application Ser. No. 11/757,841 entitled: "Systems and methods for performing measurements of one or more materials," which in incorporated herein by reference. The methods and systems of the present invention can also be used for qualitative detection where the targeted cells, bacteria or spores do not need to be enumerated, and only the presence or absence of the analyte is of interest.

The isolation of targeted biological cells of interest from other components in a sample mixture is done by immunomagnetic separation in which magnetic microspheres coupled with antibodies having a specific affinity for a particular protein on the surface on the cell of interest will bind to the cell. This binding step creates a magnetically responsive aggregate that will be attracted by the magnetic field of the apparatus. Upon introduction of the sample into the imaging chamber, aggregates will be retained in the chamber due to the presence of a magnetic field while the rest of the sample will be washed away.

Figure 1:
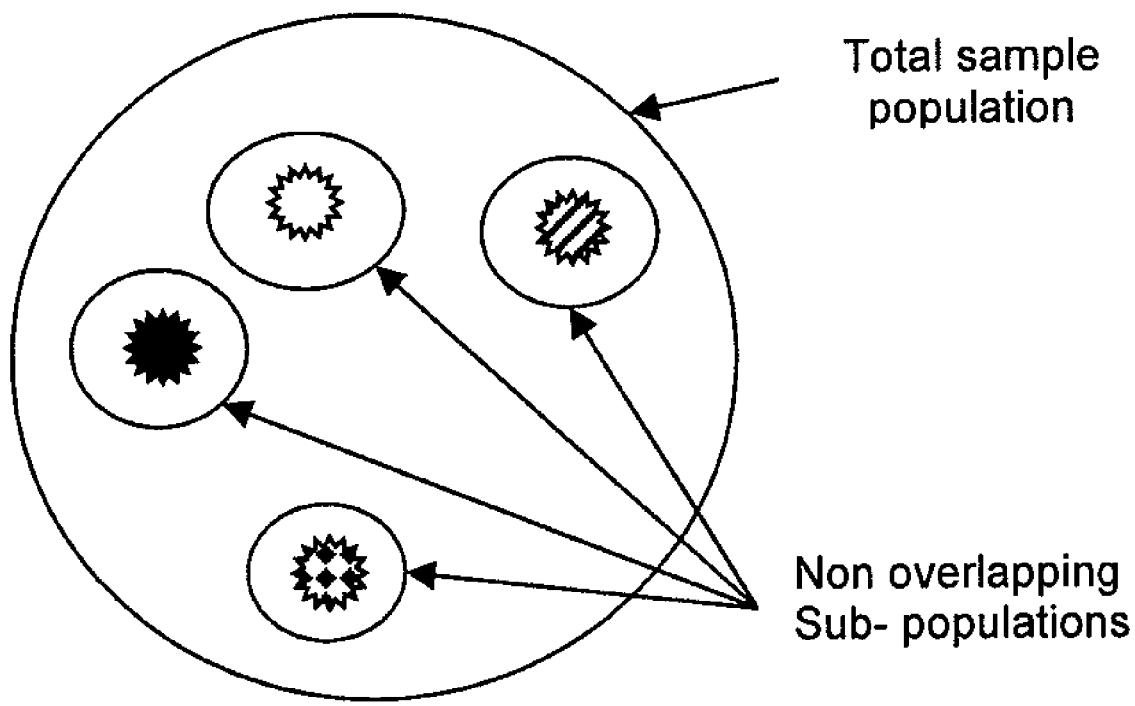
FIG. 1 shows an illustration of a sample containing multiple different cell populations. The different cell populations are indicated as white cells, black cells, striped cells, and checkered cells.
Figure 2:
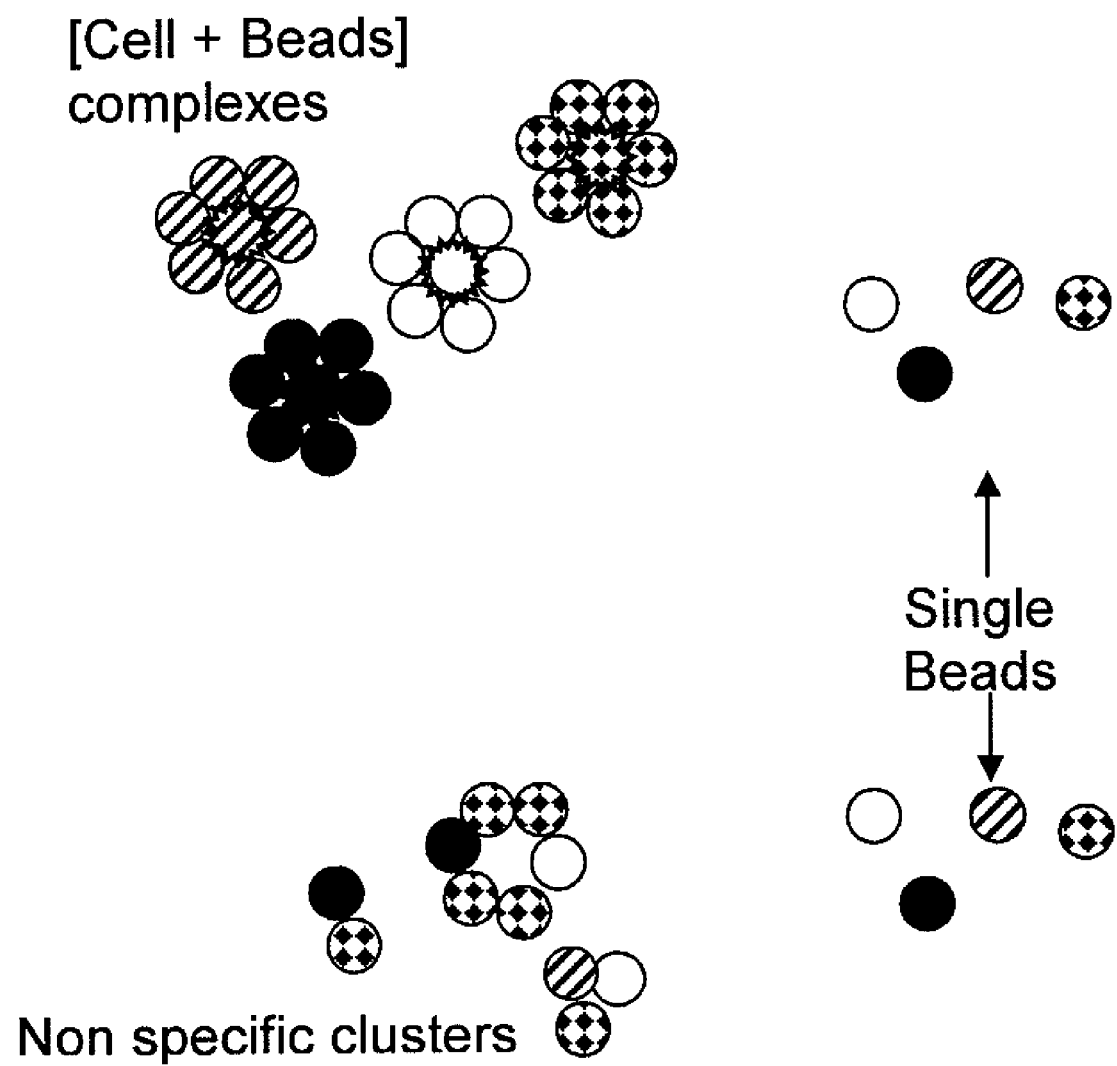
FIG. 2 illustrates four bead sets (Bead sets A (white), B (black), C (checkered), and D (striped)) that target four different cell populations. When the targeted cells are present a complex is formed among the targeted cell and the beads that bind the targeted cell. Some beads may remain single or in non-specific clusters.
Figure 4A:
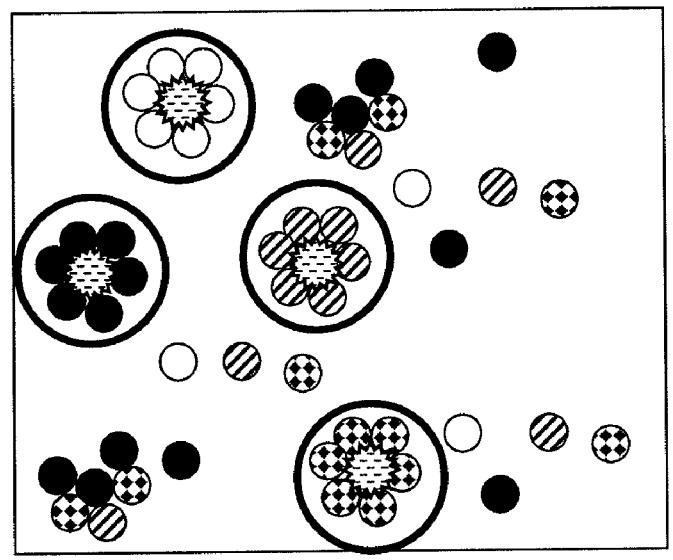
FIGS. 4A and 4B.
Figure 4B:
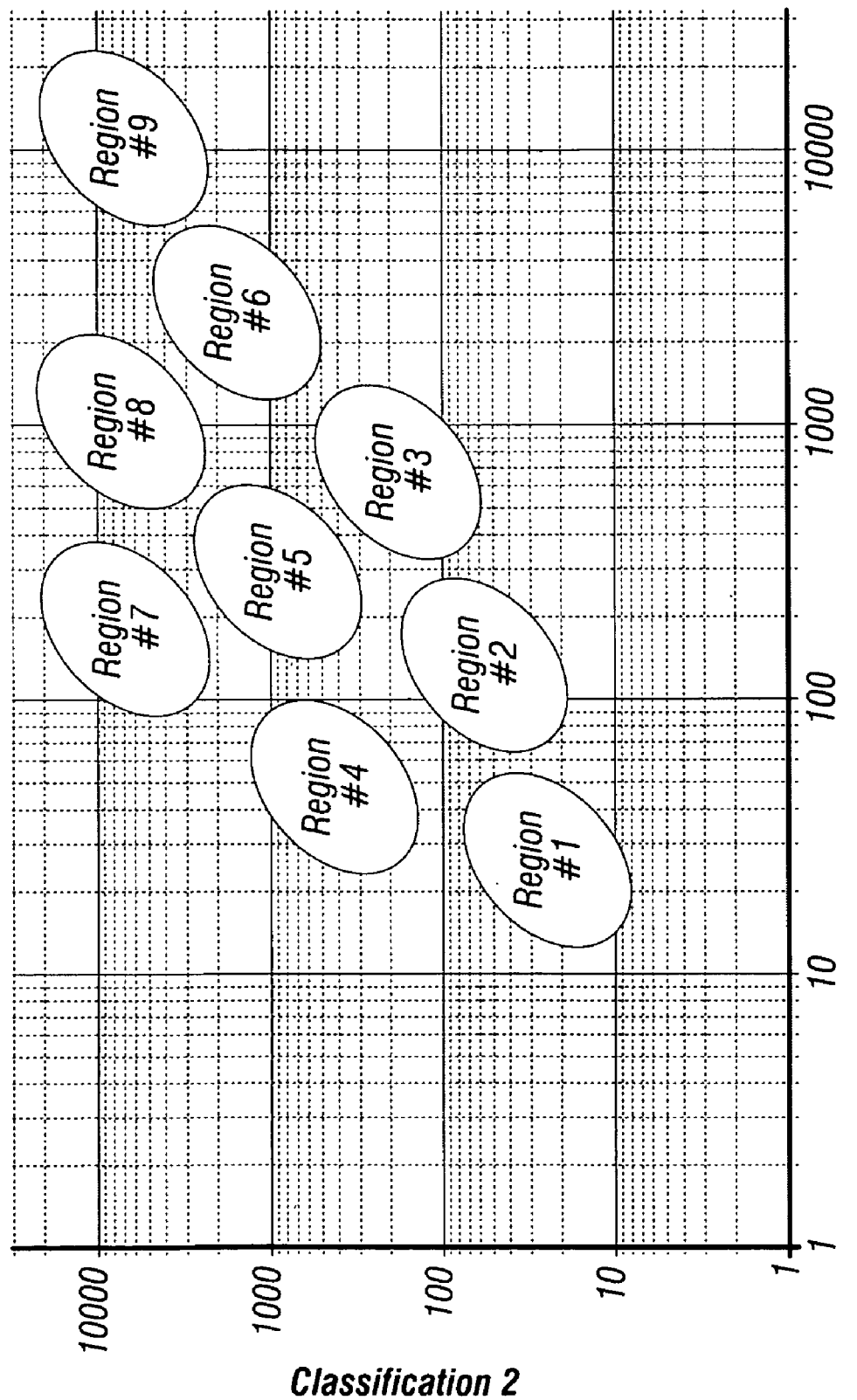

The capturing magnetic microspheres are encoded, such as with internal fluorescent dyes as describe by Chandler et al. (U.S. Pat. No. 6,773,812 and U.S. application Ser. No. 11/335,139, both of which are incorporated by reference), thus creating multiple sets of different (e.g., spectrally different) microspheres. The capturing particles may also be other magnetically responsive nanoparticles, polystyrene beads containing magnetite, latex beads containing magnetite, and any other magnetically responsive particles known by the one skilled in the art. The size of the capturing particles may range from, for example, 10 nanometers up to 100 micrometers. The use of differently coded sets of magnetic particles allows for the creation of differentiable aggregates and the multiplexed detection of different cells or biological analytes within the same sample. As illustrated in FIGS. 1 and 2, for example, multiple different cell populations in a sample may be captured using bead sets that target the different cell populations. Complexes are formed among a targeted cell and the beads that bind the targeted cell (see e.g., FIG. 2). The classification of the beads serves to identify the targeted cell, and the census of the different kind of complexes serves to enumerate the different targeted cells (see e.g., FIGS. 4A and 4B). Surprisingly, the resolution is such that numerous individual beads binding to the same cell can be distinguished. For example, 2, 3, or 4 differently labeled beads could be used to label 2, 3, or 4 different antigens on the surface of a single cell. This greatly increases the multiplexing capability of the assay. Moreover, it can render unnecessary the time-consuming process of depleting undesired cell types from the sample prior to analysis as required by conventional methods. The removal of the magnetic field allows for a complete wash and regeneration of the imaging chamber. The magnetic field may be removed from the chamber by, for example, moving the magnet away from the chamber or, if the magnet is an electromagnet, by turning the magnet off.

Figure 3:
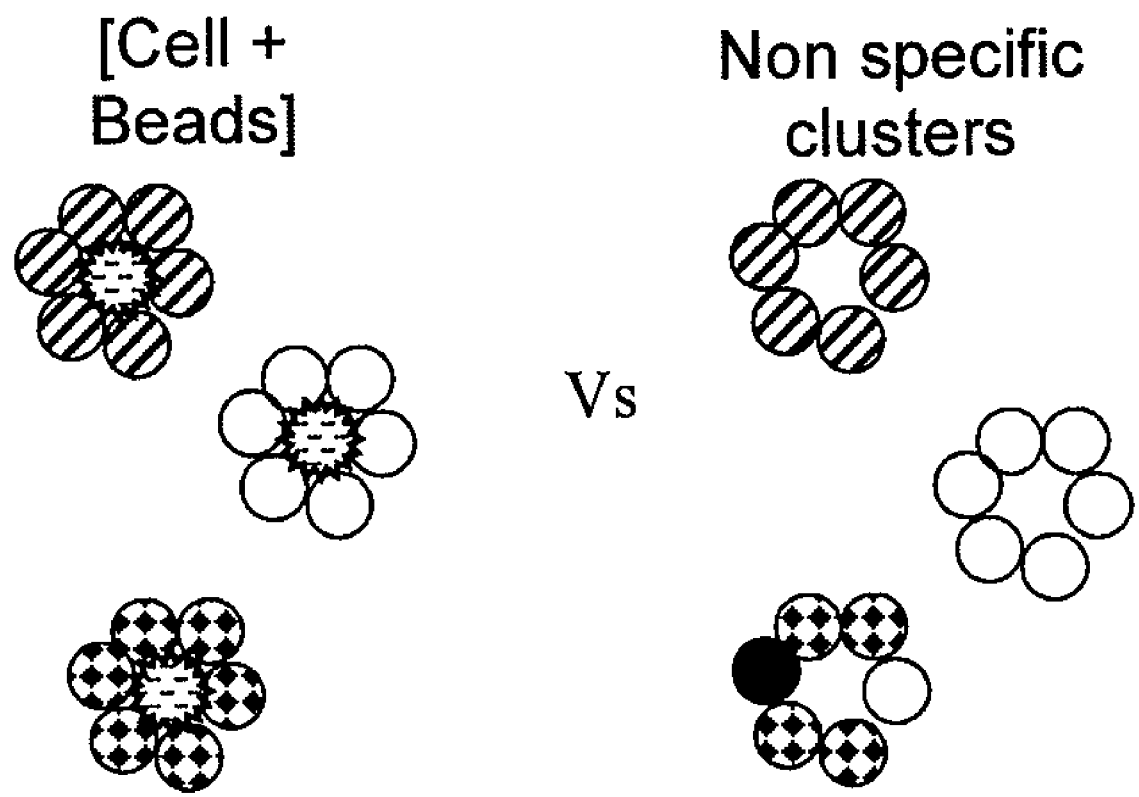
FIG. 3 illustrates an embodiment in which cells are generically stained (e.g., a nucleic acid stain) (dashed cells) to assist in the differentiation between non-specific clusters of beads that do not contain a cell and specific complexes of beads that do include a cell.

In order to differentiate a cluster of beads around a cell of interest from a nonspecific cluster of beads (no cells captured within the cluster), the use of a generic reporter dye that would stain any cell's membrane (e.g. Gram stain) or cell's nuclei (e.g. DAPI) can be included in the method (see e.g., FIG. 3). In this embodiment, the detection process will include a classification step to characterize the Median Fluorescent Intensity (MFI) of the cluster and a reporter step to ensure that a cell is within the cluster.

The specific affinity of the magnetic microsphere for the targeted biological analyte is due to reactive moieties such as antibodies coupled onto the surface of the microspheres. Other agents of specific affinity that may be used include aptamers, nucleic acid probes such as DNA or RNA, proteins, or any other molecule, natural or synthesized, that binds specifically to a target analyte of interest and that is known to the ones skilled in the art.

If beads are added to the sample at too high of a concentration and/or the beads are incubated with the sample for too long, then the number of beads binding to each cell may become too high to distinguish each individual bead. If cells are to be bound by two or more differently labeled beads, then the assay conditions should be adjusted, such as by reducing the concentration of beads and/or reducing the incubation time, until individual beads can be detected. On the other hand, if the assay is set up such that each cell type is being bound by only one bead type, then the ability to specifically identified each head is not necessary because the captured cluster can be analyzed as an aggregate. Because these captured clusters are not all identical and are comprised of a different number of beads around the cell (or bacteria or spore), the CVs for the MFI of each populations of clusters can be quite large and thus require a wide region in the classification map. The objects that are identified, imaged and characterized are not the cells themselves, but instead they are clusters comprised of multiple encoded beads around a cell. The clusters formed can be identified according to their fluorescent signature. Two examples of modes of classification are the LUMINEX® xMAP® Classification map approach (classification based on 2 colors and multiple intensities) and the multicolor classification approach (classification based on color only). With the LUMINEX® xMAP® Classification map approach, the magnetic beads used to form the cluster around the target cells may be LUMINEX® MAGPLEX® beads. Individual beads are encoded using different ratios of 2 dyes and are classifiable on the existing LUMINEX® xMAP®. Clusters formed with one kind of beads may still express a wide range of fluorescent intensities depending on the number of beads that formed the clusters. For example, a cluster formed of 6 beads may show a low fluorescent intensity, while a cluster formed with 10 to 15 beads may show a much higher fluorescence. Therefore the range of possible fluorescent intensities for a cluster made of only one kind of beads will be quite large.

The classification of the clusters into 2 fluorescent detection channels can be illustrated by a 2 dimensional map, where each axis represents a detection channel. Each cluster will fluoresce in each of the two detection channel and will have defined fluorescent intensity. The range of possible intensities for each cluster will define a region in the map. The multiplexing capability of this approach resides in the ability to define distinct regions within the map, each region being representative of a different cluster.

With the multicolor classification approach, beads are differentiated only by color (spectral characteristic) and not by intensity. The level of multiplexing will then be defined by the number of detection channels achievable by the hardware. This approach will enable the identification of clusters comprised of different kind of beads. Each color (or detection channel) will represent a dimension. Clusters (or the target cells) will be identified (characterized) according to their fluorescence (or lack of) in each detection channel. In this approach, because of the multidimensional (n>3) characterization scheme, the classification of the cluster into defined two dimensional regions (a map) is not possible. Clusters will simply be classified according to their response in each channel (a binary response such as positive or negative, 1 or 0, etc.).

The magnification of the imaging instrument can be modified and optimized for the detection of cells, spores or bacteria of different sizes: the bigger the analyte the less the needed magnification. The limiting factor for the detection of the target is the resolution of the overall optical path. Because the bead clusters typically will have a size at least 3 times larger than individual beads, the magnification of the imaging system could be reduced compared to a system designed to image beads individually. A reduced magnification will enable a larger field of view, a larger measured sample and therefore more accurate enumeration results. When multiple analytes on a cell are being targeted by differently labeled beads, then a system designed to image beads individually is preferred.

The concentrations of the cells in the sample may be calculated from the number of clusters within the field of view of the imaging chamber, the total volume of sample loaded in the apparatus, the ratio of the area of the field of view to the total area of the imaging chamber, and the capture efficiency. Once the clusters are being loaded into the imaging chamber, they will be captured do to the presence of the magnetic field. For a specific application, the system and method should be characterized in such a way that the capture efficiency of the apparatus for clusters will be known. In addition, the imaging chamber should be fully characterized as well in such a way that the imaged field of view will represent a known subset of the total surface area of the chamber. The image processing algorithms enable the enumeration of clusters within the field of view and will correlate this number with the volume of the sample introduced. Concentrations are calculated based on the sample volume and the cluster census.

The total volume of sample loaded in the chamber can be known due to the use of, for example, a precise syringe pump to pull the sample into a sample loop and to inject it into the main drive fluid line. This dual line approach enables the real-time dilution of the sample in order to slow down sample introduction but also to lower sample viscosity and improve capture efficiency. The drive fluid is in a buffer solution capable of diluting the sample. The drive fluid can be the same buffer as the washing buffer. By merging the sample line into the main drive fluid line, the drive fluid will effectively dilute the sample and carry it to the imaging chamber. Modifying the speed at which the sample is merged into the main drive fluid line will result into a different dilution factor. This enables the efficient loading of different volumes of sample, in particular small volumes. The capture efficiency represents the percentage of cells captured in the chamber from the total number of cells loaded in the chamber. There are several factors influencing the capture efficiency including: the number of receptors (or markers) available on the surface of the cell of interest; the number of magnetic beads around the cell of interest, which is related to the number of receptors available; the affinity of the antibody for a specific receptor as well as the incubation time, the concentration of the reagents etc.; the strength of the magnetic field; the size and depth of the chamber; the viscosity of the sample; and the velocity of the sample when traveling through the chamber. There are two independent objectives related to capture efficiency: maximization and characterization.

As used herein, "capture efficiency" is defined as the ratio: Number of cells detected/Actual number of cells loaded. Maximizing the capture efficiency will enable the use of a smaller sample size. It will lower the limit of detection for qualitative assays (such as the detection of anthrax spores in environmental samples) where the objective is to detect the presence or absence of a certain cell, bacteria or spore, and not to quantify a concentration within the sample. By forcing the sample into a smaller imaging chamber, the probability of having the analyte of interest in the field of view increases and therefore the limit of detection improves. Other factors influencing the capture efficiency include the size of the magnetic beads used to form clusters. Large beads will contain more magnetite but will also be submitted to stronger shear forces when moving toward the imaging surface. Smaller beads will contain less magnetite, however, less steric hindrance will enable more beads around the cell and more efficient packing of these beads. This could result in more magnetite around the cell and more compact clusters.

For quantitative assays, the output of the measurement will include a concentration of the cells in the sample. In this instance, the capture efficiency needs to be characterized and consistent in order to be able to correlate the number of cells detected to the actual number of cells in the sample. The capture efficiency of the cells can be characterized and measured by using a standard sample with a known amount of cells, loading the sample into the imaging chamber, and measuring how many cells can be detected. The detected number of cells can then be compared to the actual numbers of cells to calculate the capture efficiency. An alternate method, based on the traditional analytical method of "the added volumes," involves making aliquots of the sample and adding to each sub-sample a known amount of standard solution before any sample processing step. The measurements of each sub-sample will enable the creation of a standard curve that will include the capture efficiency (and any other variations in the sample processing protocol, or from the sample matrix) in its intrinsic parameter. The extrapolation of the standard curve toward a sample with no added standard solution will give access to the cell concentration in the sample. This method will be of particular interest for samples where the cell concentration is so low that even if the entire sample is loaded, there would not be enough cells captured to be statistically significant. By adding a known amount of cells and creating a standard curve, this method enables the measurements of a concentration below the threshold defined by more conventional methods.

The imaging chamber also has an impact on the ability to efficiently capture biological targets, and its design can be tailored to specific applications. For applications where the total sample size is minimal and where the potential number of biological targets to be capture is also low, the capture efficiency may be increased by using an imaging chamber with minimal dimensions. A small width and length of the chamber will mean that the captured biological targets will be dispersed on a smaller imaging surface, which will increase the density of cells within the field of view. In addition a small depth of the chamber will subject biological targets to a lower gradient of magnetic forces and will keep the overall sample closer to the magnet. The closer the biological targets will be to the magnet, the stronger the attractive force of the magnetic field will be and the higher the capture efficiency will become. Thus, an imaging chamber with minimal dimensions will be a chamber of a size that maximizes the density of biological targets in the field of view and subjects the sample in the chamber to the strongest attractive force of the magnetic field while not having dimensions so minimal that the captured biological targets can not be accommodated in the chamber. For example, if the clusters (e.g., cell plus beads) are expected to be around 20 nm in diameter, then an imaging chamber of minimal dimension would have a depth (where depth refers to the dimension of the chamber that is perpendicular to the magnet) of about 50 to 100 nm. Additionally, the width of such a chamber would be at least about 50 nm. For applications where the sample size can be quite large and where a qualitative response is sufficient, the imaging chamber can be designed with larger dimensions in order to process more sample within the same time frame and without having to increase the velocity of the sample introduction. For example, an imaging chamber with a depth and width of about 400 nm×400 nm may be used.

The image processing algorithm converts raw images of the field of view into a number of biological targets. Each fluorescent object in the field of view will be identified against the background signal. Then each object may be characterized in terms of size (number of pixel wide and number of pixel long), roundness (define as the ratio of the square perimeter of the object divide by (4×Pi×Area of the object), and/or other measurement of interest deemed necessary (diameter, area, radius etc. . . ). With this approach, non-specific fluorescent objects of random size and shape may be excluded from the total enumeration count. All remaining objects are included in the biological target count.

Once the initial detection and enumeration process is performed, an iterative process may be started before calculating a final concentration of cell in the sample. In this way, the number of cells counted may be above a certain threshold to be considered statistically significant. A lower threshold of 30 is often used because normal distribution statistical analysis can be performed for sample sizes above 30 cells. However, other lower thresholds, such as 35, 40, 45, or 50 cells, can be used in order to minimize the impact of image processing and measurements errors. As an upper limit, the threshold can be defined by a predetermined number of biological targets, such as 100, 200, 300, 400, 500, or 1000 cells. The threshold can also be defined according to the number of doublets present in the field of view: as the number of biological targets in the field of view increases, the probability of having two biological targets overlapping increases and doublets are suddenly more and more present. When the population of doublets is not linear anymore with the sample size being loaded, the upper limit threshold can be defined as reached.

When the number of biological targets is below the lower threshold, the image processing algorithm will command for the loading of additional sample. Then the algorithm will resume to the enumeration step again. This iterative process will take place until the number of biological targets in the field of view will reach a pre-determined lower threshold but will not be above the upper threshold. Alternatively, the counts from separate enumerations, with a complete wash of the imaging chamber between enumerations, can be saved and then added together until the minimum threshold is met. If the upper threshold is exceeded, then the magnetic filed may be removed from the imaging chamber, the imaging chamber cleaned (e.g., by pushing drive/wash fluid through a by-pass line and through the chamber), and a smaller aliquot of the sample loaded into the imaging chamber. The final enumeration step will serve as the basis for any further calculation of concentration of cells.

If multiple populations and/or subpopulations of biological targets are analyzed simultaneously, the calculations described in the previous paragraphs will be repeated for each detection channel used and for each population of encoded particles. In each calculation, the capture efficiency of the biological targets may be the same or different. In any case, like in single-plex mode, the capture efficiency needs to be characterized to enable a calculation of concentration of biological targets in the sample.

A. Imaging Systems

FIGS. 5-10 are illustrative of various apparatus on which the methods described herein may be performed. It is noted that the figures are not drawn to scale. In particular, the scale of some of the elements of the figures is exaggerated to emphasize characteristics of the elements. Elements shown in more than one figure that may be similarly configured have been indicated using the same reference numerals. It is further noted that the description of these apparatus is illustrative only and is for the purpose of teaching those skilled in the art the general manner of carrying out the invention. Further modifications and alternative embodiments will be apparent to those skilled in the art in view of this description.

Figure 5A:
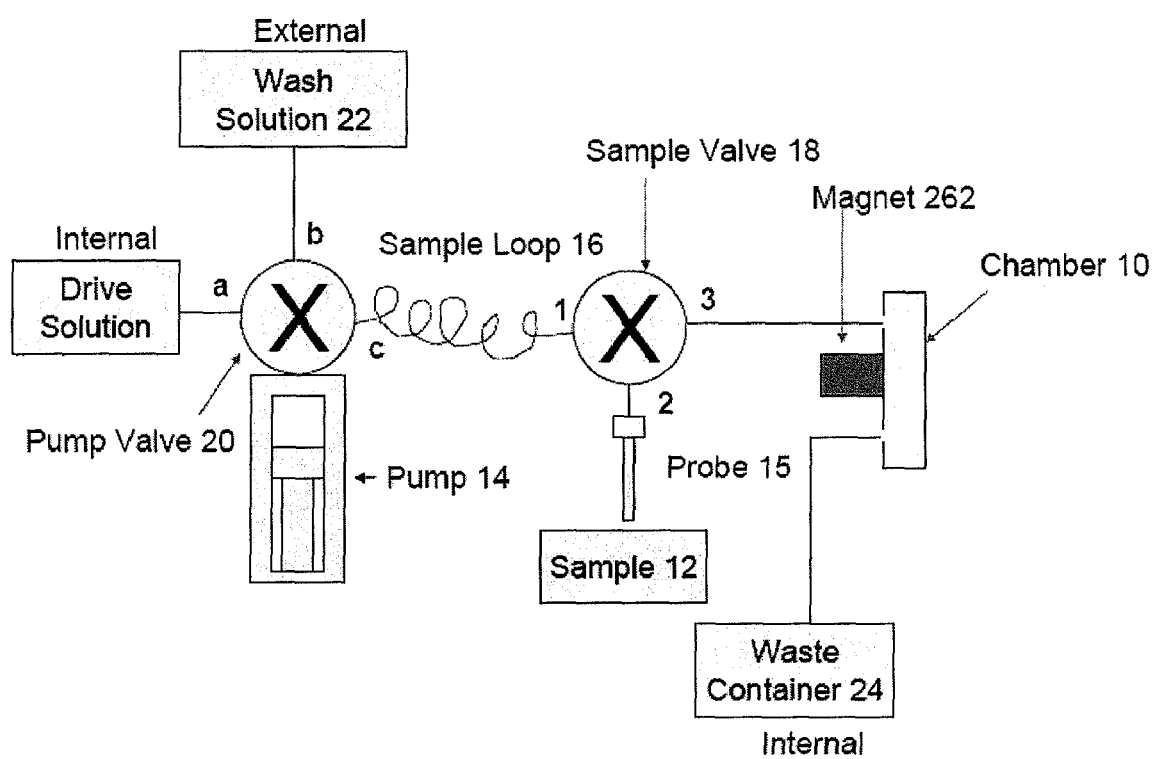
FIGS. 5A, 5B, and 5C show block diagrams of fluid handling systems.
Figure 5B:
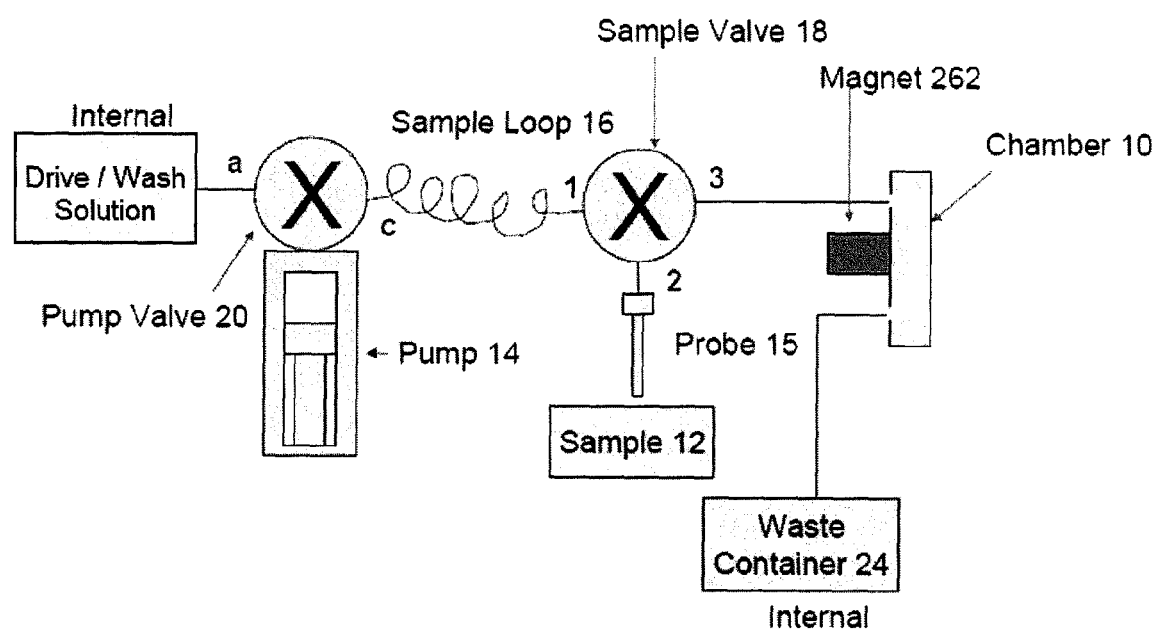
Figure 5C:
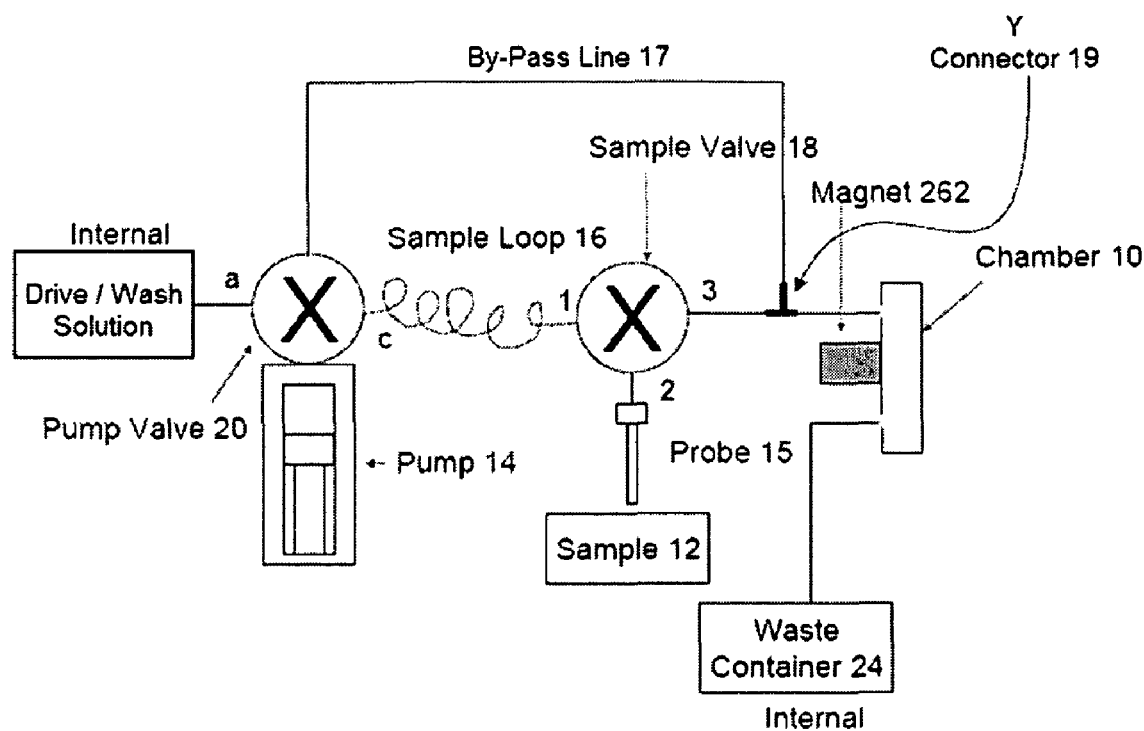
Figure 6:
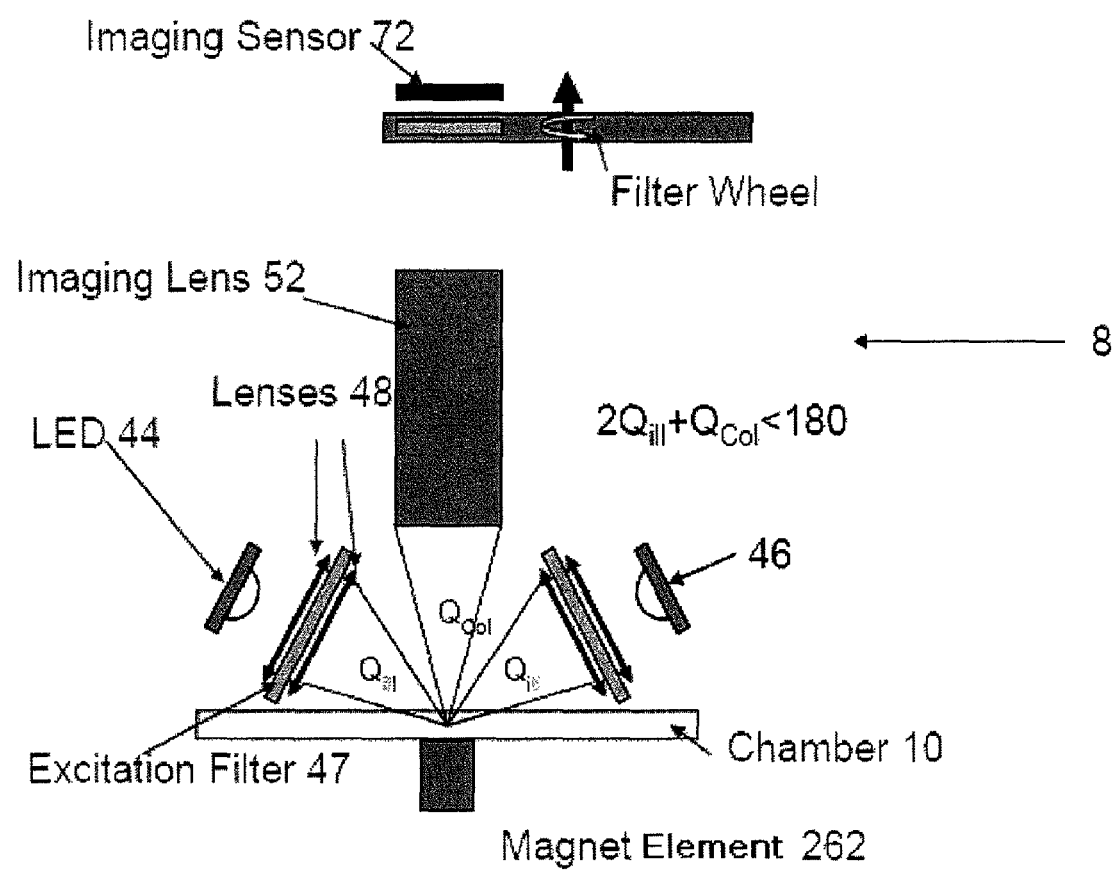
FIG. 6 shows a block diagram of the optical configuration of the imaging device.

The embodiments illustrated in FIGS. 5A-C and 6 relates generally to systems configured to transfer one or more materials to an imaging volume of a measurement device from one or more storage vessels. The systems have three major components: fluid handling, optic configuration, and particle immobilization subsystem. FIGS. 5A-C show the functional components of the fluid handling subsystem in three configurations, while FIG. 6 illustrates the functional components of the optics subsystem.

In the fluid handling subsystem of FIG. 5A-C, samples are transferred into imaging volume 10 of the measurement device from sample storage vessel 12. The imaging volume may be configured as an imaging chamber 10, which may have any suitable configuration known in the art. Storage vessel 12 may be configured as a Vacutainer, centrifuge tube, injection syringe, micro titer plate or any other suitable sample container known in the art.

The system also includes a bi-directional pump 14 configured to draw fluid into a storage reservoir and to later expel fluid from the storage reservoir into the imaging volume of chamber 10. Pump 14 may have any suitable configuration known in the art. Since the beads/biological target clusters are substantially immobilized during the exposure time as described further herein, pulse-free flow such as that obtained from an expensive syringe pump is not required. A sufficient reservoir can be formed out of a length of tubing 16 between pump 14 and sample valve 18. Such a reservoir is commonly called a "sample loop." The tubing may have any suitable configuration. The function of sample valve 18 is to connect a sample probe 15 to the reservoir (sample loop 16) when aspirating from sample storage vessel 12 and to connect the reservoir to the imaging chamber 10 when dispensing. Sample valve 18 may include any suitable valve known in the art.

Pump valve 20 is utilized at the pump end of the storage reservoir (Sample Loop 16). In FIG. 5A, pump valve 20 is connected to a drive solution storage vessel and a wash solution storage vessel. This configuration can be used if a drive solution and wash solution of different compositions are desired. However, the same solution may be used as the drive solution and the wash solution, in which case one storage vessel may be used. FIGS. 5B and 5C show pump valve 20 connected to a drive/wash solution storage vessel. FIG. 5C shows a by-pass line 17 that allows the wash of imaging chamber 10 after the introduction of a portion of the sample without having to use sample loop 16 where the rest of the sample is stored. The by-pass line thus enables the sequential loading of small aliquots from the same sample in sample loop 16 in order to accommodate for different sample concentrations and to extend the dynamic range of the method. Without by-pass line 17, washing and then loading additional sample in imaging chamber 10 involves a complete flush of sample loop 16 and then a further pickup of sample from sample storage vessel 12 to reload sample loop 16—while this approach is functional, it is less efficient and wastes more sample as compared to using a by-pass line. Pump valve 20 may include any suitable valve known in the art. In alternative embodiments, the pump and wash valves could be combined into a single valve. Pump 14 may also be configured to transfer the one or more materials and any other fluid in imaging chamber 10 to waste vessel 24. Waste vessel 24 may have any suitable configuration known in the art.

There are three primary modes of operating the fluid handling subsystem illustrated in FIGS. 5A-C to load a sample in the imaging chamber 10, namely a load procedure with sample wash, a load procedure without sample wash, and an iterative load procedure. In the fluid handling subsystem shown in FIG. 5A, the load procedure with no sample wash generally occurs as follows:

Clean System:
1) Pump Valve 20 to position a.
2) Load Drive Solution.
3) Pump Valve 20 to position c.
4) Sample Valve 18, move from position 1 to 3.
5) Move magnet 262 away from imaging chamber 10.
6) Push Drive Solution through chamber to clean chamber 10.
7) Sample Valve 18, position 1 to 2.
8) Push Drive solution through Probe 15 to clean Probe.

Load Sample:
1) Pump Valve 20 to position a.
2) Load Drive Solution.
3) Pump Valve 20 to position c.
4) Sample Valve 18, position 1 to 2.
5) Lower probe 15 into sample storage vessel 12.
6) Load a sample into sample loop 16.
7) Raise probe 15 and pull until air is at sample valve 18 and entire sample is in sample loop 16.
8) Sample Valve 18, position 1 to 3.
9) Move magnet 262 toward imaging chamber 10.
10) Push Sample from sample loop 16 into imaging chamber 10 capturing the magnetic capture agents and any biological targets and detection agents associated with them (capture complex).
11) Take Images with the capture complex is immobilized.

Clean System:
1) Pump Valve 20 to position a.
2) Load Drive Solution.
3) Pump Valve 20 to position C.
4) Sample Valve 18, position 1 to 3.
5) Move magnet 262 away from imaging chamber 10.
6) Push Drive Solution through chamber 10 to clean chamber.
7) Sample Valve 18, position 1 to 2.
8) Push Drive solution through Probe 15 to clean Probe.

In the fluid handling subsystem shown in FIG. 5A, the load procedure with sample wash generally occurs as follows:

Clean System:
1) Pump Valve 20 to position a.
2) Load Drive Solution.
3) Pump Valve 20 to position C.
4) Sample Valve 18, position 1 to 3.
5) Move magnet 262 away from chamber 10.
6) Push Drive Solution through chamber 10 to clean chamber.
7) Sample Valve 18, position 1 to 2.
8) Push Drive solution through Probe 15 to clean Probe.

Preload Wash Solution:
1) Pump Valve 20 to position b.
2) Load Wash Solution.
3) Pump Valve 20 to position c.
4) Sample Valve 18, position 1 to 3.
5) Push Wash Solution through chamber.
6) Sample Valve 18, position 1 to 2.
7) Push Wash solution through Probe 15 (sample loop 16 and probe 15 preloaded with Wash Solution).

Load Sample:
1) Pump Valve 20 to position a.
2) Load Drive Solution.
3) Pump Valve 20 to position c.
4) Sample Valve 18, position 1 to 2.
5) Lower probe 15 into well 12.
6) Load Sample into sample loop 16.
7) Raise probe 15 and pull until air is at sample valve and entire sample is in sample loop 16.
8) Sample Valve 18, position 1 to 3.
9) Move magnet 262 toward chamber 10.
10) Push Sample from sample loop 16 into chamber 10 capturing the magnetic capture agents and any biological targets and detection agents associated with them (capture complex).
11) Push Wash Solution in sample loop 16 behind sample over the capture complexes to "Wash" the capture complexes.
12) Take Images with the capture complexes immobilized.

Clean System:
1) Pump Valve 20 to position a.
2) Load Drive Solution.
3) Pump Valve 20 to position c.
4) Sample Valve 18, position 1 to 3.
5) Move magnet 262 away from chamber 10.
6) Push Drive Solution through chamber 10 to clean chamber.
7) Sample Valve 18, position 1 to 2.
8) Push Drive solution through Probe 15 to clean Probe.

In the fluid handling subsystem shown in FIG. 5A, the iterative load procedure generally occurs as follows:

Clean System:
1) Pump Valve 20 to position a.
2) Load Drive Solution.
3) Pump Valve 20 to position c.
4) Sample Valve 18, position 1 to 3.
5) Move magnet 262 away from chamber 10.
6) Push Drive Solution through chamber 10 to clean chamber.
7) Sample Valve 18, position 1 to 2.
8) Push Drive solution through Probe 15 to clean Probe.

Preload Wash Solution:
1) Pump Valve 20 to position b.
2) Load Wash Solution.
3) Pump Valve 20 to position c.
4) Sample Valve 18, position 1 to 3.
5) Push Wash Solution through chamber.
6) Sample Valve 18, position 1 to 2.
7) Push Wash solution through Probe 15 (sample loop 16 and probe 15 preloaded with Wash Solution).

Load Sample:
1) Pump Valve 20 to position a.
2) Load Drive Solution.
3) Pump Valve 20 to position c.
4) Sample Valve 18, position 1 to 2.
5) Lower probe 15 into well 12.
6) Load Sample into sample loop 16.
7) Raise probe 15 and pull until air is at sample valve and entire sample is in sample loop 16.
8) Sample Valve 18, position 1 to 3.
9) Move magnet 262 toward chamber 10.
10) Push Sample from sample loop 16 into chamber 10 capturing the magnetic capture agents and any biological targets and detection agents associated with them (capture complex).

11) Push Wash Solution in sample loop 16 behind sample over the capture complexes to "Wash" the capture complexes.
12) Take Images with the capture complexes immobilized.
13) Process images using image analysis algorithms and determine if further sample needs to be loaded. If further sample needs to be loaded, then restart loading sequence at step 1. If further sample is not needed, then proceed to "Clean System" sequence.

Clean System:
1) Pump Valve 20 to position a.
2) Load Drive Solution.
3) Pump Valve 20 to position c.
4) Sample Valve 18, position 1 to 3.
5) Move magnet 262 away from chamber 10.
6) Push Drive Solution through chamber 10 to clean chamber.
7) Sample Valve 18, position 1 to 2.
8) Push Drive solution through Probe 15 to clean Probe.

In the fluid handling subsystem shown in FIG. 5B, the load procedure with no sample wash generally occurs as follows:

Clean System:
1) Pump Valve 20 to position a.
2) Load Drive/Wash Solution.
3) Pump Valve 20 to position c.
4) Sample Valve 18, move from position 1 to 3.
5) Move magnet 262 away from imaging chamber 10.
6) Push Drive/Wash Solution through chamber to clean chamber 10.
7) Sample Valve 18, position 1 to 2.
8) Push Drive/Wash Solution through Probe 15 to clean Probe.

Load Sample:
1) Pump Valve 20 to position a.
2) Load Drive/Wash Solution.
3) Pump Valve 20 to position c.
4) Sample Valve 18, position 1 to 2.
5) Lower probe 15 into sample storage vessel 12.
6) Load a sample into sample loop 16.
7) Raise probe 15 and pull until air is at sample valve 18 and entire sample is in sample loop 16.
8) Sample Valve 18, position 1 to 3.
9) Move magnet 262 toward imaging chamber 10.
10) Push Sample from sample loop 16 into imaging chamber 10 capturing the magnetic capture agents and any biological targets and detection agents associated with them (capture complex).
11) Take Images with the capture complex is immobilized.

Clean System:
1) Pump Valve 20 to position a.
2) Load Drive/Wash Solution.
3) Pump Valve 20 to position c.
4) Sample Valve 18, position 1 to 3.
5) Move magnet 262 away from imaging chamber 10.
6) Push Drive/Wash Solution through chamber 10 to clean chamber.
7) Sample Valve 18, position 1 to 2.
8) Push Drive/Wash Solution through Probe 15 to clean Probe.

In the fluid handling subsystem shown in FIG. 5B, the load procedure with sample wash generally occurs as follows:

Clean System:
1) Pump Valve 20 to position a.
2) Load Drive/Wash Solution.
3) Pump Valve 20 to position c.
4) Sample Valve 18, position 1 to 3.
5) Move magnet 262 away from chamber 10.
6) Push Drive/Wash Solution through chamber 10 to clean chamber.
7) Sample Valve 18, position 1 to 2.
8) Push Drive solution through Probe 15 to clean Probe.

Load Sample:
1) Pump Valve 20 to position a.
2) Load Drive/Wash Solution.
3) Pump Valve 20 to position c.
4) Sample Valve 18, position 1 to 2.
5) Lower probe 15 into well 12.
6) Load Sample into sample loop 16.
7) Raise probe 15 and pull until air is at sample valve and entire sample is in sample loop 16.
8) Sample Valve 18, position 1 to 3.
9) Move magnet 262 toward chamber 10.
10) Push Sample from sample loop 16 into chamber 10 capturing the magnetic capture agents and any biological targets and detection agents associated with them (capture complex).
11) Push Drive/Wash Solution in sample loop 16 behind sample over the capture complexes to "Wash" the capture complexes.
12) Take Images with the capture complexes immobilized.

Clean System:
1) Pump Valve 20 to position a.
2) Load Drive/Wash Solution.
3) Pump Valve 20 to position c.
4) Sample Valve 18, position 1 to 3.
5) Move magnet 262 away from chamber 10.
6) Push Drive/Wash Solution through chamber 10 to clean chamber.
7) Sample Valve 18, position 1 to 2.
8) Push Drive solution through Probe 15 to clean Probe.

In the fluid handling subsystem shown in FIG. 5B, the iterative load procedure generally occurs as follows:

Clean System:
1) Pump Valve 20 to position a.
2) Load Drive/Wash Solution.
3) Pump Valve 20 to position c.
4) Sample Valve 18, position 1 to 3.
5) Move magnet 262 away from chamber 10.
6) Push Drive/Wash Solution through chamber 10 to clean chamber.
7) Sample Valve 18, position 1 to 2.
8) Push Drive/Wash Solution through Probe 15 to clean Probe.

Load Sample:
1) Pump Valve 20 to position a.
2) Load Drive/Wash Solution.
3) Pump Valve 20 to position c.
4) Sample Valve 18, position 1 to 2.
5) Lower probe 15 into well 12.
6) Load Sample into sample loop 16.
7) Raise probe 15 and pull until air is at sample valve and entire sample is in sample loop 16.
8) Sample Valve 18, position 1 to 3.
9) Move magnet 262 toward chamber 10.
10) Push Sample from sample loop 16 into chamber 10 capturing the magnetic capture agents and any biological targets and detection agents associated with them (capture complex).
11) Push Drive/Wash Solution in sample loop 16 behind sample over the capture complexes to "Wash" the capture complexes.
12) Take Images with the capture complexes immobilized.
13) Process images using image analysis algorithms and determine if further sample needs to be loaded. If further sample needs to be loaded, then restart loading sequence at step 1. If further sample is not needed, then proceed to "Clean System" sequence.

Clean System:
1) Pump Valve 20 to position a.
2) Load Drive/Wash Solution.
3) Pump Valve 20 to position c.
4) Sample Valve 18, position 1 to 3.
5) Move magnet 262 away from chamber 10.
6) Push Drive/Wash Solution through chamber 10 to clean chamber.
7) Sample Valve 18, position 1 to 2.
8) Push Drive/Wash solution through Probe 15 to clean Probe.

In the fluid handling subsystem shown in FIG. 5C, the load procedure with no sample wash generally occurs as follows:

Clean System:
1) Pump Valve 20 to position a.
2) Load Drive/Wash Solution.
3) Pump Valve 20 to position c.
4) Sample Valve 18, move from position 1 to 3.
5) Move magnet 262 away from imaging chamber 10.
6) Push Drive/Wash Solution through chamber to clean chamber 10.
7) Sample Valve 18, position 1 to 2.
8) Push Drive/Wash Solution through Probe 15 to clean Probe.

Load Sample:
1) Pump Valve 20 to position a.
2) Load Drive/Wash Solution.
3) Pump Valve 20 to position c.
4) Sample Valve 18, position 1 to 2.
5) Lower probe 15 into sample storage vessel 12.
6) Load a sample into sample loop 16.
7) Raise probe 15 and pull until air is at sample valve 18 and entire sample is in sample loop 16.
8) Sample Valve 18, position 1 to 3.
9) Move magnet 262 toward imaging chamber 10.
10) Push Sample from sample loop 16 into imaging chamber 10 capturing the magnetic capture agents and any biological targets and detection agents associated with them (capture complex).
11) Take Images with the capture complex is immobilized.

Clean System:
1) Pump Valve 20 to position a.
2) Load Drive/Wash Solution.
3) Pump Valve 20 to position c.
4) Sample Valve 18, position 1 to 3.
5) Move magnet 262 away from imaging chamber 10.
6) Push Drive/Wash Solution through chamber 10 to clean chamber.
7) Sample Valve 18, position 1 to 2.
8) Push Drive/Wash Solution through Probe 15 to clean Probe.

In the fluid handling subsystem shown in FIG. 5C, the load procedure with sample wash generally occurs as follows:

Clean System:
1) Pump Valve 20 to position a.
2) Load Drive/Wash Solution.
3) Pump Valve 20 to position c.
4) Sample Valve 18, position 1 to 3.
5) Move magnet 262 away from chamber 10.
6) Push Drive/Wash Solution through chamber 10 to clean chamber.
7) Sample Valve 18, position 1 to 2.
8) Push Drive solution through Probe 15 to clean Probe.

Load Sample:
1) Pump Valve 20 to position a.
2) Load Drive/Wash Solution.
3) Pump Valve 20 to position c.
4) Sample Valve 18, position 1 to 2.
5) Lower probe 15 into well 12.
6) Load Sample into sample loop 16.
7) Raise probe 15 and pull until air is at sample valve and entire sample is in sample loop 16.
8) Sample Valve 18, position 1 to 3.
9) Move magnet 262 toward chamber 10.
10) Push Sample from sample loop 16 into chamber 10 capturing the magnetic capture agents and any biological targets and detection agents associated with them (capture complex).
11) Pump Valve 20 to position a.
12) Load Drive/Wash Solution.
13) Pump Valve 20 to position b.
14) Push Drive/Wash Solution through By-Pass Line 17 and over the capture complexes in Image Chamber 10 to "Wash" the capture complexes.
15) Take Images with the capture complexes immobilized.

Clean System:
1) Pump Valve 20 to position a.
2) Load Drive/Wash Solution.
3) Pump Valve 20 to position c.
4) Sample Valve 18, position 1 to 3.
5) Move magnet 262 away from chamber 10.
6) Push Drive/Wash Solution through chamber 10 to clean chamber.
7) Sample Valve 18, position 1 to 2.
8) Push Drive solution through Probe 15 to clean Probe.

In the fluid handling subsystem shown in FIG. 5C, the iterative load procedure generally occurs as follows:

Clean System:
1) Pump Valve 20 to position a.
2) Load Drive/Wash Solution.
3) Pump Valve 20 to position c.
4) Sample Valve 18, position 1 to 3.
5) Move magnet 262 away from chamber 10.
6) Push Drive/Wash Solution through chamber 10 to clean chamber.
7) Sample Valve 18, position 1 to 2.
8) Push Drive/Wash Solution through Probe 15 to clean Probe.

Load Sample:
1) Pump Valve 20 to position a.
2) Load Drive/Wash Solution.
3) Pump Valve 20 to position c.
4) Sample Valve 18, position 1 to 2.
5) Lower probe 15 into well 12.
6) Load Sample into sample loop 16.
7) Raise probe 15 and pull until air is at sample valve and entire sample is in sample loop 16.
8) Sample Valve 18, position 1 to 3.
9) Move magnet 262 toward chamber 10.
10) Push Sample from sample loop 16 into chamber 10 capturing the magnetic capture agents and any biological targets and detection agents associated with them (capture complex).
11) Pump Valve 20 to position a.
12) Load Drive/Wash Solution.
13) Pump Valve 20 to position b.
14) Push Drive/Wash Solution through By-Pass Line 17 and over the capture complexes in Image Chamber 10 to "Wash" the capture complexes.
15) Take Images with the capture complexes immobilized.

16) Process images using image analysis algorithms and determine if further sample needs to be loaded. If further sample needs to be loaded in chamber 10, then restart loading sequence at step 10 if additional Sample is still contained in sample loop 16 or at step 1 if additional Sample needs to first be loaded into sample loop 16. If further sample is not needed in chamber 10, then proceed to "Clean System" sequence.

Clean System:
1) Pump Valve 20 to position a.
2) Load Drive/Wash Solution.
3) Pump Valve 20 to position c.
4) Sample Valve 18, position 1 to 3.
5) Move magnet 262 away from chamber 10.
6) Push Drive/Wash Solution through chamber 10 to clean chamber.
7) Sample Valve 18, position 1 to 2.
8) Push Drive/Wash solution through Probe 15 to clean Probe.

An advantage of using the second and third loading procedures where the sample is "washed" is to remove from the surrounding solution components in the sample that are not immobilized by the magnetic field. For the convenience of processing, some assays do not perform the wash step.

The optics subsystem 8 is broadly illustrated in FIG. 6. Subsystem 8 includes magnetic element 262 positioned on the side of imaging chamber 10 opposite the optics of the system. Magnetic element 262 may include any suitable magnetic element known in the art such as a permanent magnet or an electromagnet that can be used to generate a suitable magnetic field. In this manner, biological targets bound to magnetic particles can be substantially immobilized in imaging chamber 10 using a magnetic field generated by magnetic element 262 at the side of the chamber. Although magnetic element 262 is shown adjacent to imaging chamber 10 in FIG. 6, the magnetic element may be coupled to imaging chamber 10, integral in imaging chamber 10, or spaced from the imaging chamber 10. In addition, although FIG. 6 shows one magnetic element positioned proximate the imaging chamber, it is to be understood that the system may include more than one magnetic element.

After signal acquisition by the measurement device, the magnetic field may be removed (e.g., by using a solenoid to move a permanent magnet or by turning an electromagnet on and off with a switch), and the biological targets and magnetic beads may exit the imaging chamber 10.

The simplest imaging chamber 10 design is an imaging chamber that has a relatively smooth internal surface on the side of the imaging chamber proximate the magnetic element such that the beads are randomly distributed across this internal surface as the magnet 262 pulls them to the surface. However, the imaging chamber 10 can also be designed to "hold" the capture complexes in particular spots when the magnetic field is applied as described in more detail herein.

With the capture complexes immobilized in the chamber 10, the illumination module (LEDs 44, 46) is operated to excite encoded magnetic bead, which in this embodiment is internally labeled with a fluorophore. The imaging sensor 72 (CCD) captures the image and the image is processed (See, e.g. U.S. patent application Ser. No. 11/534,166 entitled "Methods and Systems for Image Data Processing" filed Sep. 21, 2006 by Roth, which is incorporated by reference herein.) The magnet 262 releases the sample and the device is cleaned.

The position of the imaging sensors 72 in relation to the LEDs 44, 46, chamber 10 and magnet 262 can be adjusted for imaging biological targets in accordance with the present invention. In this embodiment, the beads have distinct characteristics, namely different wavelengths and intensities of internal fluorescent dyes, that absorb and re-emit photons in no preferred direction (uniformly over all angles). The positions of the illumination by the LED's 44, 46 and imaging sensors (CCD 72) is chosen to optimize the "angle space" of any beads bound to biological targets in the Field of View (FOV) of the imaging sensors (CCD 72). Since the magnet 262 is on the back of the chamber 10, the angle space available for the illumination and imaging systems is a hemisphere above the magnet. The more coverage over this illumination angle space by the illumination optics (LEDs 44, 46), the more power imparted on the beads during imaging. Similarly, the higher the collection angle (Numerical Aperture) over the illumination angle space, the more flux the imaging lens 52 (FIG. 6) can collect and deliver to the imaging sensor 72 (CCD detector). A balance must be made between the angles allocated for the imaging sensors and the illumination system.

For low-cost manufacturability, the imaging lens 52 practical limit for numerical aperture is around 0.3 for a magnification of 4. For higher magnifications, the numerical aperture of imaging lens 52 could increase while maintaining the same cost guidelines. Other factors that effect the cost of the lens 52 are Field of View and broadness of waveband. A numerical aperture of 0.3 is roughly 35 degrees full angle.

For the positioning of the illumination module, e.g. the LEDs 44, 46, the limit may be the LED's brightness as well as the cost of the excitation filters 47. The etendue of the LED will dictate what of the detection agent's angle space is needed to provide the maximum LED flux over the field of view (FOV). (Etendue is the Area of the source multiplied by the solid angle of the source: it defines the geometry characteristics of the emitted flux.) If the FOV is relatively large, the angle space required will be lower and therefore more LEDs can be used.

Figure 7:
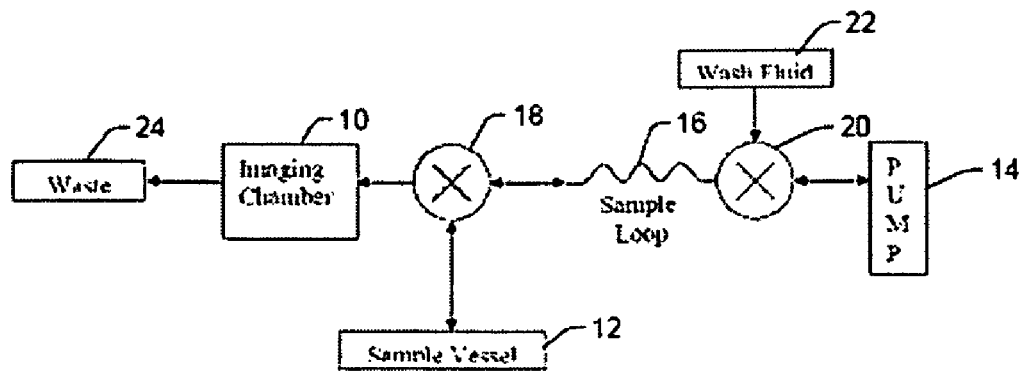
FIG. 7 shows a block diagram of an imaging system.

Another embodiment of such a system in accordance with the present invention is shown in FIG. 7. In this embodiment, samples are transferred into imaging volume 10 from storage vessel 12. The system also includes single bi-directional pump 14 configured to draw fluid into a storage reservoir and to later expel fluid from the storage reservoir into the imaging volume. Pump 14 may have any suitable configuration known in the art. Since the capture complexes are substantially immobilized during the exposure time as described further herein, pulse-free flow such as that obtained from an expensive syringe pump is not required for the system embodiments described herein. A sufficient reservoir can be formed out of a length of tubing 16 between pump 14 and sample valve 18. Such a reservoir is commonly called a "sample loop." Wash valve 20 is utilized at the pump end of the storage reservoir to allow fresh water (or other suitable reagent) from storage vessel 22 to flow to the imaging volume. Wash valve 20 may include any suitable valve known in the art. Note that the sample and wash valves could be combined into a single valve (not shown). Pump 14 may also be configured to transfer the one or more materials and any other fluid in imaging volume 10 to waste vessel 24. Waste vessel 24 may have any suitable configuration known in the art.

Figure 8:
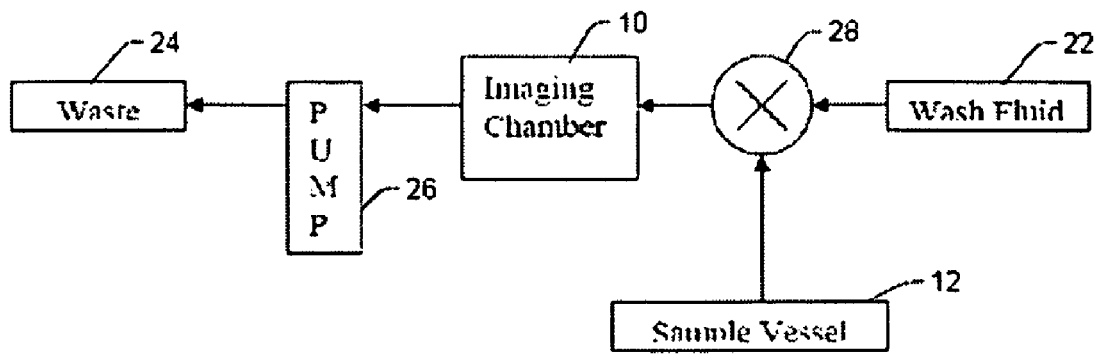
FIG. 8 shows a block diagram of an imaging system.

Another embodiment of a system configured to transfer one or more materials to an imaging volume of a measurement device from one or more storage vessels is shown in FIG. 8. In this configuration, the system includes pump 26 configured to draw liquid directly into imaging volume 10 from sample vessel 12 and then out to waste vessel 24. Pump 26 may include any suitable pump known in the art such as a peristaltic pump. Imaging volume 10, sample vessel 12, and waste vessel 24 may be configured as described above. Optional valve 28 between sample vessel 12 and wash fluid vessel 22 and imaging volume 10 may be configured to change positions depending on whether sample is to be transferred to the imaging volume or if wash fluid is to be transferred to the imaging volume (e.g., if the wash function is to be performed). Valve 28 may include any suitable valve known in the art. In addition, storage vessel 22 may be configured as described above. The embodiment shown in FIG. 8 differs from the embodiment shown in FIG. 7 since this embodiment does not include a temporary reservoir, includes one less valve, and utilizes a pump configured to move fluids in only one direction.

Figure 9:
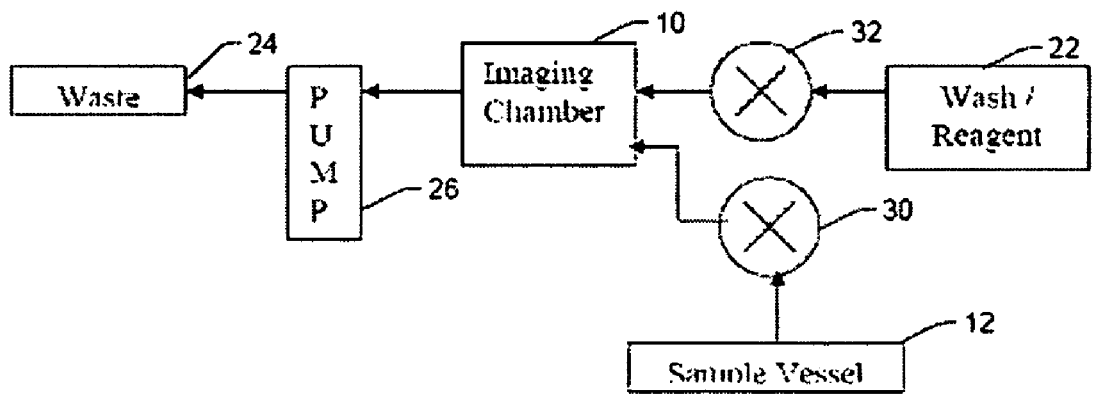
FIG. 9 shows a block diagram of an imaging system.

An additional embodiment of a system configured to transfer one or more materials to an imaging volume of a measurement device from one or more storage vessels is shown in FIG. 9. This embodiment has a configuration that is similar to the configuration of the embodiment shown in FIG. 8, with the exception that sample/wash valve 28 of the embodiment shown in FIG. 8 is replaced by two valves 30 and 32. Valves 30 and 32 may include any suitable valves known in the art. For example, valves 30 and 32 may include open/closed type valves configured to separately and simultaneously allow fluid from storage vessels 12 and 22, respectively, to be transferred into imaging volume 10. Storage vessels 12 and 22 and imaging volume 10 may be configured as described herein.

Providing separate wash and sample paths (i.e., one path from storage vessel 12 to imaging volume 10 and another separate path from storage vessel 22 to imaging volume 10) in this manner makes it possible to achieve all of the aspects of the embodiment shown in FIG. 8 and adds the ability to mix wash fluid and/or one or more reagents to the sample to be measured as the sample is transferred into imaging volume 10. Mixing wash fluid and/or one or more reagents to the sample as the sample is transferred to the imaging volume may be performed to dilute the sample such that the capture complexes are distributed farther apart within the imaging volume (e.g., farther apart on the surface of the imaging chamber).

Figure 10:
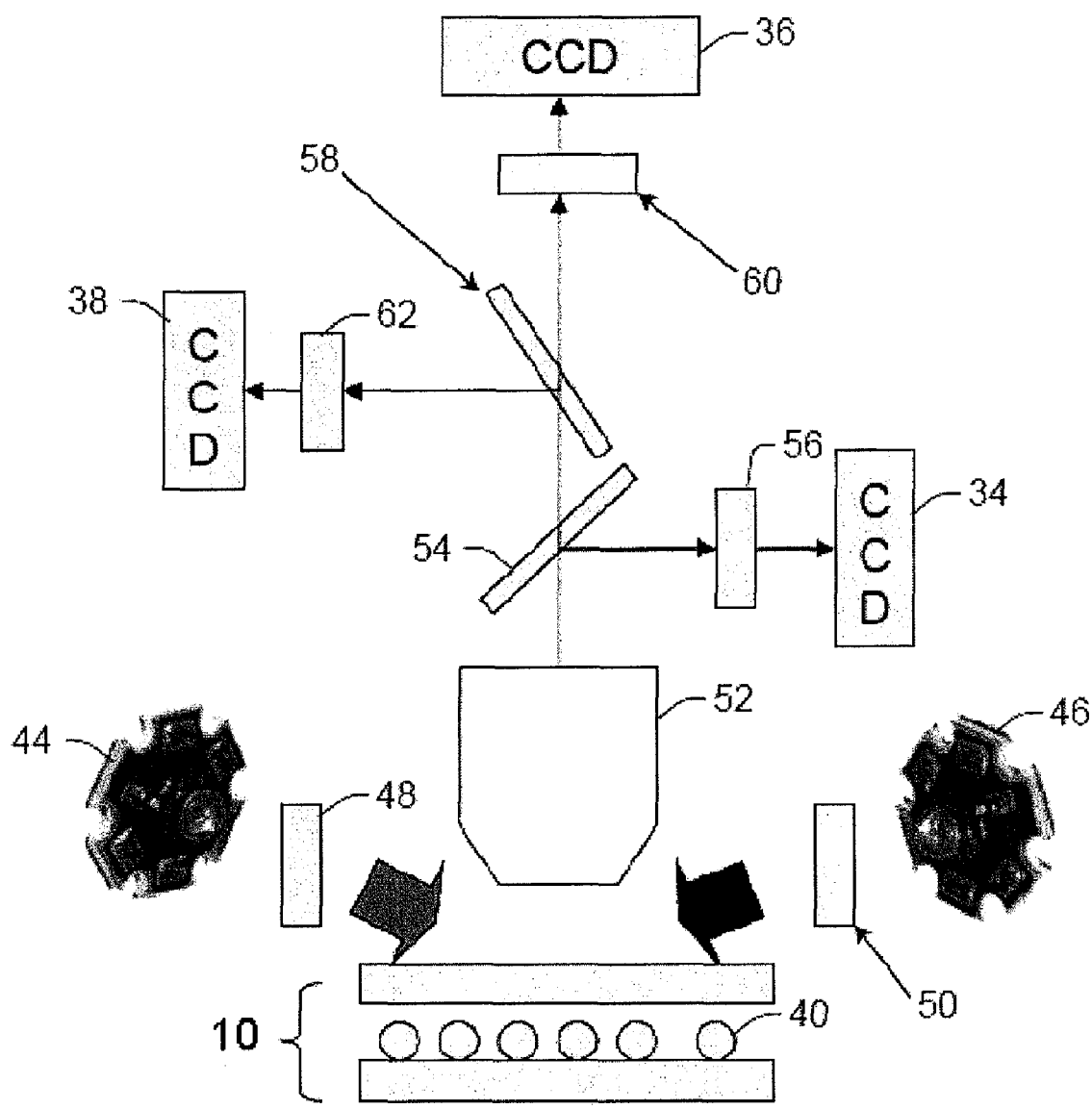
FIG. 10 is a schematic diagram illustrating a side view of the imaging system.

FIG. 10 illustrates one embodiment of a system configured to image one or more materials in an imaging volume of a measurement device. This system embodiment includes detectors 34, 36, and 38. Detectors 34, 36, and 38 may be CCD cameras or any other suitable imaging devices known in the art. Each of the detectors may have the same configuration or different configurations. Each of the detectors may be configured to detect light (e.g., light fluoresced from capture complexes 40 in imaging volume defined by imaging chamber 10) at a different wavelength or wavelength band. In addition, each of the detectors may be configured to generate images or "capture fluorescent pictures" of capture complexes 40 in imaging chamber 10.

The system also includes light sources 44 and 46 configured to emit light having different wavelengths or different wavelength bands (e.g., one of the light sources may be configured to emit red light and the other light source may be configured to emit green light). The light emitted by light sources 44 and 46 may include, for example, light in any part of the visible wavelength spectrum. Light sources 44 and 46 may include LEDs or any other suitable light sources known in the art. Light sources 44 and 46 are arranged above the periphery of imaging chamber 10. In addition, the light sources are arranged above the imaging chamber such that each light source directs light to capture complexes 40 in imaging chamber 10 at different directions.

The system also includes filters 48 and 50 coupled to light sources 44 and 46, respectfully. Filters 48 and 50 may be bandpass filters or any other suitable spectral filters known in the art. In this manner, the system may use light sources 44 and 46 and filters 48 and 50 to sequentially illuminate the capture complexes with different wavelengths or different wavelength bands of light.

The system may also include lens 52 positioned at the center (or approximately the center) of the illumination "ring." Lens 52 may include any suitable refractive optical element known in the art. Lens 52 is configured to image light scattered and/or fluoresced from the capture complexes onto one or more monochrome CCD detector(s) (e.g., detectors 34, 36, and 38) via one or more optical elements, which may include one or more dichroic and one or more optical bandpass filters. For example, light exiting lens 52 is directed to dichroic filter 54, which may include any suitable dichroic optical element known in the art. Dichroic filter 54 is configured to reflect light of one wavelength or wavelength band and to transmit light of other wavelengths or wavelength bands. Light reflected by dichroic filter 54 is directed to filter 56, which may be a bandpass filter or other suitable spectral filter. Light exiting filter 56 is directed to detector 34.

Light transmitted by lens 52 may also be directed to dichroic filter 58, which may include any suitable dichroic optical element known in the art. Dichroic filter 58 may be configured to reflect light of one wavelength or wavelength band and to transmit light of other wavelengths or wavelength bands. Light transmitted by dichroic filter 58 is directed to filter 60, which may be a bandpass filter or other suitable spectral filter. Light exiting filter 60 is directed to detector 36. Light reflected by dichroic filter 58 is directed to filter 62, which may be a bandpass filter or other suitable spectral filter. Light exiting filter 62 is directed to detector 38. Furthermore, although the system shown in FIG. 10 includes two light sources, it is to be understood that the system may include any suitable number of light sources. Additionally, although the system shown in FIG. 10 includes three detectors configured to image light scattered and/or fluoresced from the capture complexes at different wavelengths or wavelength bands, it is to be understood that the system may include two or more detectors. For example, the system may include two or more CCD detectors (and optionally fixed filters) that can be used to simultaneously measure the classification channel(s) and reporter channel(s) thereby providing higher throughput for the measurements.

The system shown in FIG. 10 is, therefore, configured to generate a plurality or series of images representing the fluorescent emission of capture complexes 40 at several wavelengths of interest. In addition, the system may be configured to supply a plurality or series of digital images representing the fluorescence emission of the capture complexes to a processor (i.e., a processing engine). The system may or may not include the processor (not shown). The processor may be configured to acquire (e.g., receive) image data from detectors 34, 36, and 38. For example, the processor may be coupled to detectors 34, 36, and 38 in any suitable manner known in the art (e.g., via transmission media (not shown), each coupling one of the detectors to the processor, via one or more electronic components (not shown) such as analog-to-digital converters, each coupled between one of the detectors and the processor, etc.).

The processor may be configured to process and analyze these images to, for example, classify and enumerate the captured biological target(s). This information may be output by the processor in any suitable format such as a data array with an entry for fluorescent magnitude for each capture complex for each wavelength. Specifically, the processor may be configured to perform one or more steps of a method for processing and analyzing the images. Examples of methods for processing and analyzing images generated by a system such as that shown in FIG. 10 are illustrated in U.S. patent application Ser. No. 11/534,166 entitled "Methods and Systems for Image Data Processing" filed Sep. 21, 2006 by Roth, which is incorporated by reference herein. The systems described herein may be further configured as described in this patent application. In addition, the methods described herein may include any step(s) of any of the method(s) described in this patent application.

For example, in one embodiment the processor may be configured to analyze the images to detect and enumerate the biological targets (e.g., cells) that are labeled and immobilized on the surface of the chamber by binding the encoded magnetic beads, and determine whether a statistically significant number of the labeled biological targets are immobilized on the surface of the chamber. The processor is configured such that it then prompts the addition of more sample into the chamber if a statistically significant number of the labeled biological targets were not immobilized on the surface of the chamber. The processor repeats the detection, enumeration, determination, and sample addition process until a statistically significant number of the labeled biological targets are immobilized on the surface of the chamber. The processor then proceeds with further processing and analysis of the image(s). As mentioned above, the processor is configured such that it then prompts the addition of more sample into the chamber if a statistically significant number of the labeled biological targets were not immobilized on the surface of the chamber. The processor may prompt the addition of more sample by prompting (such as by an audible or visual signal) a user to manually inject or operate a pump to deliver additional sample to the chamber. Alternatively, the pump may be under the control of the processor such that the pump operates to deliver additional sample to the chamber by receiving a signal from the processor.

The processor may be a processor such as those commonly included in a typical personal computer, mainframe computer system, workstation, etc. In general, the term "computer system" may be broadly defined to encompass any device having one or more processors, which executes instructions from a memory medium. The processor may be implemented using any other appropriate functional hardware. For example, the processor may include a digital signal processor (DSP) with a fixed program in firmware, a field programmable gate array (FPGA), or other programmable logic device (PLD) employing sequential logic "written" in a high level programming language such as very high speed integrated circuits (VHSIC) hardware description language (VHDL). In another example, program instructions (not shown) executable on the processor to perform one or more steps of the computer-implemented methods described in the above-referenced patent application may be coded in a high level language such as C#, with sections in C++ as appropriate, ActiveX controls, JavaBeans, Microsoft Foundation Classes ("MFC"), or other technologies or methodologies, as desired. The program instructions may be implemented in any of various ways, including procedure-based techniques, component-based techniques, and/or object-oriented techniques, among others.

Program instructions implementing methods such as those described in the above-referenced patent application may be contained in a computer-readable medium such as a read-only memory, a random access memory, a magnetic or optical disk, or a magnetic tape.

B. Antibodies

Methods for preparing and characterizing antibodies are well known in the art. Briefly, a polyclonal antibody is prepared by immunizing an animal with an immunogen comprising a polypeptide of interest and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

The immunogenicity of a particular immunogen composition can be enhanced by the use of non-specific stimulators of the immune response, known as adjuvants. Exemplary adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196, 265, incorporated herein by reference. Typically, this technique involves immunizing a suitable animal with a selected immunogen composition. The immunizing composition is administered in a manner effective to stimulate antibody producing cells. Rodents such as mice and rats are commonly used for monoclonal antibody production.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody producing B lymphocytes from the immunized animal are then fused with cells of an immortal myeloma cell, generally one of the same species as the animal that was immunized. Myeloma cell lines suited for use in hybridoma producing fusion procedures preferably are non-antibody producing, have high fusion efficiency, and enzyme deficiencies that render then incapable of growing in certain selective media which support the growth of only the desired fused cells (hybridomas).

Methods for generating hybrids of antibody producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion procedures usually produce viable hybrids at low frequencies. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas are then serially diluted and cloned into individual antibody producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

C. Aptamers

Aptamers are nucleic acid sequences that are designed through repeated rounds of selection to bind to various molecular targets such as small molecules, proteins, nucleic acids, and even cells, tissues and organisms. Aptamers offer molecular recognition properties that rival those of antibodies. In addition, aptamers offer advantages over antibodies as they can be engineered completely in vitro, are readily produced by chemical synthesis, and possess desirable storage properties. Aptamers are typically created by the SELEX (Systematic Evolution of Ligands by Exponential Enrichment) process and variations upon it. The SELEX process is described in, for example, U.S. Pat. Nos. 5,270,163 and 5,475,096 (both of which are incorporated by reference).

D. Immuno-Magnetic Separation

Immuno-magnetic separation (IMS) is a technique used to separate biological cells from their matrix. The technique uses magnetic microspheres with antibodies that will selectively attach to a target cell. The complex formed by the microsphere and the cell is then selectively removed from the sample matrix through the use of a magnetic field. IMS can be used to deplete a sample from a specific cell type or to select a specific cell type from a sample. The method can also be used to concentrate a sample with the target cell type. For instance, with conventional assays the enumeration of CD4 T-cells from peripheral blood for patients infected with HIV requires depleting the blood sample of the population of monocytes that also carry the CD4 protein on their surface and that will falsely increase the number of CD4 T lymphocytes. The depletion of monocytes is done by selective separation using magnetic beads coupled to an anti-CD14 antibody specific to monocytes. Another example of IMS application is the removal of tumor cells from the marrow of patients who are undergoing autologous bone marrow transplantation. Other examples of IMS are described in Olsvik Orjan et al. "Magnetic separation techniques in diagnostic microbiology", Clinical Microbiology reviews, January 1994, p 43-54.

DYNABEADS® are a well-established line of superparamagnetic particles used in a wide variety of applications including cell isolation, either positive or negative, cell expansion, protein sample preparation, protein isolation etc. DYNABEADS® can be used in a direct or indirect method. In a direct method, the target cell will directly attach to the beads via a specific antibody coupled to the bead. In an indirect method, the cell will first form a complex with a free primary antibody specific to the target. Then the complex will be captured using a bead coupled to a secondary antibody targeting the primary antibody. The advantages of the indirect method are: first to enable a better binding of the primary antibody to the target cell by taking advantage of the small size of the antibody and avoiding steric hindrance due to the size of the bead; second to compensate for the disadvantage of the steric hindrance due to size of the magnetic bead by using a complex with a high affinity constant (such as Biotin-Avidin) to form the bound between the secondary and primary antibody. The inconvenience of the indirect method are that two incubation times are needed instead of one for the direct method. Also the method is not suited for a multiplex detection scheme because the secondary antibody is not specific to the target cell (e.g. CD4) but instead is a specific against the species of the primary antibody (Mouse, goat etc...).

The DYNABEADS® enable the positive isolation of cells where the target cell is first captured by the magnetic beads and then is released through the use of specific reagents. This approach results in the isolation of cell while maintaining its complete integrity and keeping it suitable for further downstream applications. Other types of isolation include negative isolation, or depletion, where the target cell is purified by removing part or all other cell types. Application for DYNABEADS® include isolation of human cell subsets such as B lymphocytes, endothelial cells, granulocytes, hematopoietic progenitor cells, Langherhans cells, neural cells, natural killer cells, T lymphocytes including CD3, CD4 and CD8 T-cells. Dynal: "Cell separation and protein purification" Dynal Technical Handbook; 2nd Edition, 1996. DYNABEADS®, however, are not used for the identification of the cell to which they attach. Consequently there is no multiplexing capability with the Dynal technology.

E. Encoded Magnetic Particles

Although certain embodiments are described herein with respect to encoded microspheres (i.e., beads), it is to be understood that the illumination subsystems, systems, and methods may also be used with other encoded magnetic particles. The particles are preferably superparamagnetic. Examples of encoded microspheres, beads, and particles are illustrated in U.S. Pat. No. 5,736,330 to Fulton, U.S. Pat. No. 5,981,180 to Chandler et al., U.S. Pat. No. 6,057,107 to Fulton, U.S. Pat. No. 6,268,222 to Chandler et al., U.S. Pat. No. 6,449,562 to Chandler et al., U.S. Pat. No. 6,514,295 to Chandler et al., U.S. Pat. No. 6,524,793 to Chandler et al., and U.S. Pat. No. 6,528,165 to Chandler, which are incorporated by reference herein. Excitation of dyes or fluorochromes within or on the surface of encoded particles may be accomplished by laser light, diode light, arc lamp, heat, radioactive emission, chemiluminescence, electroluminescence, chemielectroluminescence, or any other method known to those skilled in the art.

In certain embodiments, the present invention is used in conjunction with LUMINEX® xMAP® and MAGPLEX® technologies. The LUMINEX® xMAP® technology allows the detection of nucleic acid products immobilized on fluorescently encoded microspheres. By dyeing microspheres with 10 different intensities of each of two spectrally distinct fluorochromes, 100 fluorescently distinct populations of microspheres are produced. Digital signal processing allows the translation of signals into real-time, quantitative data. The LUMINEX® technology is described, for example, in U.S. Pat. Nos. 5,736,330, 5,981,180, and 6,057,107, all of which are specifically incorporated by reference. LUMINEX® MAGPLEX® microspheres are superparamagnetic microspheres that are fluorescently encoded using the xMAP® technology discussed above. The microspheres contain surface carboxyl groups for covalent attachment of biomolecules.

F. Kits

Any of the compositions described herein may be comprised in a kit. The kits may comprise suitably aliquoted encoded magnetic beads coupled to antibodies (or other capture agents), as may be used to isolate, separate, or detect a targeted cell or population of cells. The components of the kits may be packaged either in aqueous media or in lyophilized form. The kit may also include one or more buffers, such as hybridization buffer or a wash buffer. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional containers into which the additional components may be separately placed. However, various combinations of components may be comprised in a vial. The kits of the present invention also will typically include a means for containing the encoded magnetic beads coupled to antibodies (or other capture agents) and any other reagent containers in close confinement for commercial sale. Such containers may include cardboard or injection or blow-molded plastic containers into which the desired vials, bottles, etc. are retained.

When the components of the kit are provided in one or more liquid solutions, the liquid solution may be an aqueous solution, with a sterile aqueous solution being particularly preferred.

However, certain components of the kit may be provided as dried powder(s). When reagents and/or components are provided as a dry powder, the powder can be reconstituted by the addition of a suitable solvent. It is envisioned that the solvent may also be provided in another container means.

A kit may also include instructions for employing the kit components. Instructions may include variations that can be implemented.

G. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Enumeration of CD4 and CD8 Lymphocytes

In this example, a sample of whole blood is first depleted of its monocyte population using an anti-CD14 antibody. Then using two sets of LUMINEX® MAGPLEX® magnetic beads, CD4 cells and CD8 cells are immuno-magnetically isolated in the imaging chamber of the instrument and separated from the rest of the sample. Subsequent detection and analysis of the clusters enable the characterization and enumeration of the captured cells.

A sample of whole blood is collected and stored in a BD Vacutainer containing 2 mM EDTA as anticoagulant (BD Biosciences #366452). LUMINEX® MAGPLEX® beads (set #1) are coated with anti-CD4 antibody using a two-step carbodiimide coupling protocol per the manufacturer's instructions. LUMINEX®

MAGPLEX® beads (set #2) are coated with anti-CD8 antibody using the two-step carbodiimide coupling protocol per the manufacturer's instructions.

The blood sample is depleted of monocytes using standard immunomagnetic separation techniques and an anti-CD14 antibody. 20 µL of the sample is pipeted into a 1.5 mL centrifuge tube. The equivalent of 500,000 MAGPLEX® beads from set #1 (specific for CD4 cells) is added directly to the sample. The equivalent of 500,000 MAGPLEX® beads from set #2 (specific for CD8 cells) is added directly to the sample. A nucleic acid stain is added to stain the cells. Some mixing is performed using the pipetor. The sample is incubating for 20 minutes without further mixing steps.

The sample is diluted using 1 mL of a solution of PBS/BSA (Prepackaged PBS/BSA: Sigma P3688) and presented to the injection syringe of the imaging apparatus. An aliquot of the sample is injected into the imaging chamber. The magnetic field of the apparatus is turned on as soon as the sample introduction is started. Successive visualization of the sample and introduction of new sample aliquots enable the decision of continuing loading more sample aliquots or ending this step. Once the loading step is completed, individual beads and clusters of beads within the field of view are analyzed using image processing algorithms. Individual beads are identified according to their shape, size, and fluorescent intensity. Individual beads are characteristic of the excess of capturing reagent used, as well as the coupling efficiency with the targeted cells. An excess of beads compared to the number of cells ensure that practically one bead will not simultaneously bind to multiple cells.

Beads and nucleated cells are identified by their fluorescent signals. The resolution is such that each cell and all of the beads bound to the cell can be individually identified. In some instances, however, the number of beads binding a single cell may be large enough that only a cluster of beads can be observed. This is not a problem in studies where each cell type is bound by only one bead type, as the clusters of beads will be identified according to their size and shape. Clusters of interest have a size between 15 to 24 microns, a roundness close to 1 and display median fluorescent intensity values within region 1 or 2 defined in the classification map. These clusters are included in the enumeration of the cells they are targeting. Other non-specific bead aggregates such as doublets triplet or non specific multiplets will display random size, shapes and median fluorescent intensities. These non-specific aggregates will be discarded from any cell count.

Example 2

Enumeration and Classification of Etiologic Agent in Septic Patients

In this example, a sample of whole blood from a suspected septic patient is collected. Using a series of LUMINEX® MAGPLEX® beads coupled to bacterial species-specific capture antibodies, bacterial cells present in the blood are isolated in the imaging chamber of the instrument and separated from the rest of the sample. Captured cells are identified and enumerated.

A sample of whole blood is collected and stored in a BD Vacutainer containing 2 mM EDTA as anticoagulant (BD Biosciences #366452). LUMINEX® MAGPLEX® bead sets 1-8 are coated with antibodies directed against the following bacteria using a two-step carbodiimide coupling protocol per the manufacturer's instructions: *Escherichia coli, Listeria monocytogenes, Neisseria meningitides, Streptococcus pneumoniae, Staphylococcus aureas, Haemophilus influenzae, Pseudomonas aeruginosa, and Streptococcus Pyogenes*. LUMINEX® MAGPLEX® beads (set #9) are coated with anti-CD61 antibody (platelet cell surface marker) using the two-step carbodiimide coupling protocol per the manufacturer's instructions.

The blood sample is depleted of monocytes using standard immunomagnetic separation techniques and an anti-CD14 antibody. 50 µL of the sample is pipeted into a 1.5 mL centrifuge tube. The equivalent of 100,000 MagPlex beads from each set are added directly to the sample. The sample is incubating for 20 minutes with gentle mixing (end over end). The sample is diluted using 1 mL of a solution of PBS/BSA (Prepackaged PBS/BSA: Sigma P3688) and presented to the injection syringe of the reading prototype. An aliquot of the sample is injected into the imaging chamber. The Magnetic field of the apparatus is applied as sample introduction begins. Sample loading volume is optimized for cell density and separation in viewing field. After sample application, wash fluid is run through the sample loop and over the immobilized sample to remove debris. Once the loading step is completed, individual beads and clusters of beads within the field of view are analyzed using image processing algorithms. Identification and enumeration of bacterial cells are compared to enumerated platelet counts to determine bacterial load.

Example 3

Enumeration of CD4 and CD8 Lymphocytes without Monocyte Depletion

In this example, CD4 and CD8 lyphocytes in a sample of whole blood are analyzed without first depleting the monocyte population. A sample of whole blood is collected and stored in a BD Vacutainer containing 2 mM EDTA as anticoagulant (BD Biosciences #366452). LUMINEX® MAGPLEX® beads (set #1) are coated with anti-CD4 antibody using a two-step carbodiimide coupling protocol per the manufacturer's instructions. LUMINEX® MAGPLEX® beads (set #2) are coated with anti-CD8 antibody using the two-step carbodiimide coupling protocol per the manufacturer's instructions. LUM1NEX® MAGPLEX® beads (set #3) are coated with anti-CD14 antibody using the two-step carbodiimide coupling protocol per the manufacturer's instructions.

20 µL of the sample is pipeted into a 1.5 mL centrifuge tube. The equivalent of 500,000 MAGPLEX® beads from each of sets #1 (specific for CD4 cells), set #2 (specific for CD8 cells). and set #3 (specific for CD14 cells) are added directly to the sample. Some mixing is performed using the pipetor. The sample is incubating for 20 minutes without further mixing steps.

The sample is diluted using 1 mL of a solution of PBS/BSA (Prepackaged PBS/BSA: Sigma P3688) and presented to the injection syringe of the imaging apparatus. An aliquot of the sample is injected into the imaging chamber. The magnetic field of the apparatus is turned on as soon as the sample introduction is started. Successive visualization of the sample and introduction of new sample aliquots enable the decision of continuing loading more sample aliquots or ending this step. Once the loading step is completed, individual beads and clusters of beads within the field of view are analyzed using image processing algorithms. Individual beads are identified according to their shape, size, and fluorescent intensity. Accordingly, CD4 and CD8 lymphocytes are identified by their binding to beads of sets #1 and #2. Monocytes, which also express CD4, can be distinguished from CD4 lymphocytes because the monocytes will also bind bead set #3 (specific for CD14).

Example 4

Capture Specificity, Efficiency, and Multiplex Capability

A simulated cell capture was performed in which an antibody coupled to one LUMINEX® MAGPLEX® bead region was the capturing agent and a second bead region was the target entity. By using a magnetic bead instead of a cell as a target entity, "uncaptured" targets (defined as a target beads not bound to a capture bead) could also be isolated and identified, which was useful for the measurement of the capture efficiency. The specificity of the capture was evaluated using a control where the target entity was a magnetic bead coupled to Bovine Serum Albumin (BSA), an unrelated protein and irrelevant target.

The capture beads and the target beads were incubated together at 4° C. under gentle rotation. For each assay, one aliquot was analyzed after one hour of incubation and another aliquot was analyzed after 5 hours of incubation. The samples were analyzed with a Nikon 2000 fluorescent microscope using a combined bottom white illumination and a fluorescent excitation. During the image analysis, the beads were classified as follows:
  Single targets attached to up to 4 capture beads were classified as "captured targets."
  Single targets not attached to any beads were classified as "uncaptured targets."
  Single or multiple targets clustered with multiple capture beads were consider "irresolvable aggregates."

Figure 11:
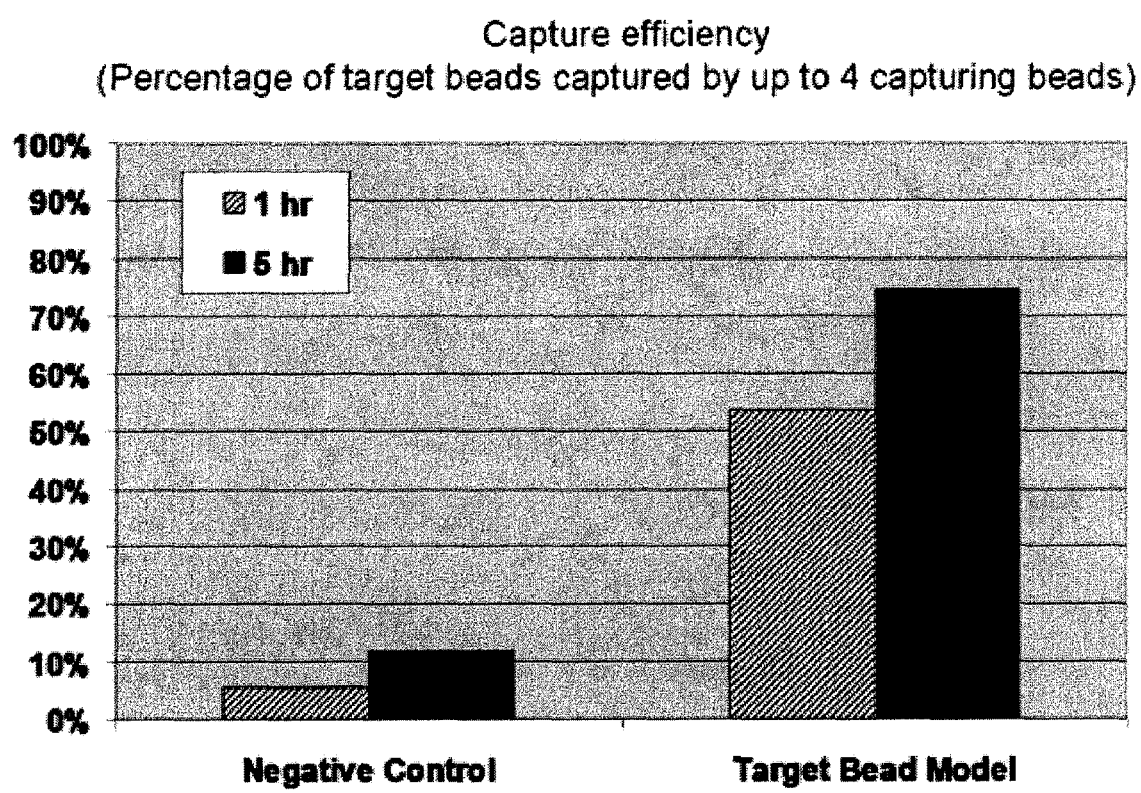
FIG. 11 shows the capture efficiency of the target bead and a negative control after 1 and 5 hours of incubation.

The capture efficiency was defined as the "captured targets" divided by the sum of "uncaptured and captured targets." The capture efficiency did not account for target beads that formed irresolvable aggregates and only considered those target beads that could be individually identified and enumerated. The result of this experiment showed that the capture efficiency was 54% after one hour of incubation, and 74% after 5 hours of incubation (FIG. 11).

The specificity of the capture was demonstrated by comparing the positive simulation to the negative control experiment. While after an hour of incubation, more than 50% of the target beads were captured in the simulation model, only 6% of them were captured in the negative control. After 5 hours of incubation, a similar specificity was observed (FIG. 11).

To achieve full multiplex potential, the assay conditions need to be such that an optimum number of beads will bind around the target cell. Not enough microspheres around the cell (less than 1 microsphere per cell) would result in many cells not being captured and not being accounted for. While this is acceptable for diagnostic assays that are just trying to establish the presence of certain kinds of cells, bacteria or spores in a sample ("Yes" or "No" assays), a low capture efficiency will not be suitable for applications requiring a full census of the target cells. On the other hand, too many microspheres around the cells would result in large clusters of beads around the target cells or in large aggregates made of multiple cells and beads. This would render the decoding of individual beads much more complex and would reduce the multiplex capability of the method. Therefore for multiplex applications the optimum number of microspheres around the target cell is such that each microspheres can be individually analyzed and classified.

An analysis of the composition of the clusters including at least one target entity was performed. The clusters were identified by the number "n" of capture beads around a target entity. The results are shown for the positive assay only (Table 1).

TABLE 1

|  | 1 Hour Incubation | 5 Hour Incubation |
| --- | --- | --- |
| n = 0 | 2% | 3% |
| n = 1 | 79% | 44% |
| n = 2 | 16% | 24% |
| n = 3 | 1% | 9% |
| n = 4 | 0% | 3% |
| unresolved aggregates | 2% | 16% |

As incubation time increased, the size of the clusters increased as well. After one hour of incubation, 79% of the captured target entities are in contact with one capture bead only, and 16% are in contact with two capture beads. After 5 hours of incubation, the proportion of small clusters decreases as bigger clusters (3 and 4 capture beads around a target entity) are becoming more predominant.

* * *

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bioinformatics Market Research 2006 Report #06-030: *influencing brand preference in the flow cytometry market*
The Cell—A molecular approach; Geoffrey M. Cooper. ASM Press. 1997
"*Cell separation and protein purification*" Dynal Technical Handbook; 2nd Edition, 1996
Orjan, Olsvik et al., "*Magnetic separation techniques in diagnostic microbiology*", Clinical Microbiology Reviews, January 1994, p 43-54
U.S. Pat. No. 4,196,265
U.S. Pat. No. 5,270,163
U.S. Pat. No. 5,475,096
U.S. Pat. No. 5,736,330
U.S. Pat. No. 5,981,180
U.S. Pat. No. 6,057,107
U.S. Pat. No. 6,268,222
U.S. Pat. No. 6,449,562
U.S. Pat. No. 6,514,295
U.S. Pat. No. 6,524,793
U.S. Pat. No. 6,528,165
U.S. Pat. No. 6,632,526
U.S. Pat. No. 6,773,812
U.S. patent application Ser. No. 11/335,139
U.S. patent application Ser. No. 11/534,166
U.S. patent application Ser. No. 11/757,841

The invention claimed is:

1. A method for immobilizing and detecting a cell in a sample comprising:
   (a) introducing a sample and a first capture complex comprising an encoded magnetic bead coupled to antibodies having a specific affinity for a particular epitope on a first cell that may be present in the sample into a chamber;
   (b) applying a magnetic field to the chamber to attract magnetically responsive aggregates of the first capture complex and the first cell to a surface of the chamber; and
   (c) detecting the first cell and the encoded magnetic bead of the first capture complex in the magnetically responsive aggregates that are immobilized on the surface of the chamber.

2. The method of claim 1, further comprising enumerating the cells that are immobilized on the surface of the chamber.

3. The method of claim 2, further comprising determining whether a statistically significant number of the cells are immobilized on the surface of the chamber, and introducing an additional amount of the sample into the chamber until a statistically significant number of the cells are immobilized on the surface of the chamber.

4. The method of claim 3, further comprising determining the concentration of the cells in the sample.

5. The method of claim 1, wherein the sample is a bodily fluid.

6. The method of claim 1, wherein the sample is an environmental sample.

7. The method of claim 1, wherein the cell is a lymphocyte, leukocyte, or monocyte.

8. The method of claim 1, wherein the cell is a bacteria cell, a spore, or a fungus cell.

9. The method of claim 1, wherein the sample is contacted with the capture complex prior to introducing the sample into the chamber.

10. The method of claim 1, wherein the sample is contacted with the capture complex after introducing the sample into the chamber.

11. The method of claim 1, wherein the encoded magnetic bead is encoded with one or more fluorescent dyes.

12. The method of claim 1, further comprising contacting the sample with a second capture complex comprising an encoded magnetic bead coupled to an antibody, wherein the encoded magnetic bead of the second capture complex is spectrally distinct from the encoded magnetic bead of the first capture complex, and further wherein the antibody of the second capture complex has a specific affinity for a particular epitope on a second cell that is distinct from the first cell.

13. The method of claim 1, further comprising contacting the sample with a second capture complex comprising an encoded magnetic bead coupled to an antibody, wherein the encoded magnetic bead of the second capture complex is spectrally distinct from the encoded magnetic bead of the first capture complex, and further wherein the antibody of the second capture complex has a specific affinity for a second epitope on the first cell.

14. The method of claim 1, further comprising staining the cell with a generic reporter dye that stains cell membranes or a generic reporter dye that stains cell nuclei.

15. The method of claim 14, wherein detecting the cells comprises taking a classification image to detect a signal from the encoded magnetic beads and taking a reporter image to detect a signal from the generic reporter dye that stains the cells.

16. A method for immobilizing and detecting one or more cell populations in a sample comprising:
(a) introducing a sample, a first capture complex comprising a first encoded magnetic bead and a first antibody having a specific affinity for a particular epitope on a first cell population that may be present in the sample, and a second capture complex comprising a second encoded magnetic bead and a second antibody having a specific affinity for a particular epitope on a second cell population that may be present in the sample into a chamber;
(b) applying a magnetic field to the chamber to attract magnetically responsive aggregates of the first capture complex and the first population of cells and magnetically responsive aggregates of the second capture complex and the second population of cells to a surface of the chamber; and
(c) detecting the first population of cells and the encoded magnetic beads of the first capture complex and the second population of cells and the encoded magnetic beads of the second capture complex in the magnetically responsive aggregates that are immobilized on the surface of the chamber.

17. The method of claim 16, further comprising enumerating the first and second populations of cells.

18. The method of claim 17, further comprising determining whether a statistically significant number of the first and second populations of cells are immobilized on the surface of the chamber, and introducing an additional amount of the sample into the chamber until a statistically significant number of the first and second populations of the cells are immobilized on the surface of the chamber.

19. The method of claim 18, further comprising determining a ratio of the first population of cells to the second population of cells.

20. The method of claim 18, further comprising determining the concentration of the first population of cells in the sample.

21. The method of claim 18, further comprising determining the concentration of the second population of cells in the sample.

22. The method of claim 18, further comprising determining the concentrations of both the first and second populations of cells in the sample.

23. The method of claim 16, further comprising staining the cell populations with a generic reporter dye that stains cell membranes or a generic reporter dye that stains cell nuclei.

24. The method of claim 23, wherein detecting the cell populations comprises taking a first classification image to detect a signal from the encoded magnetic beads of the first capture complex, taking a second classification image to detect a signal from the encoded magnetic beads of the second capture complex, and taking a reporter image to detect a signal from the generic reporter dye that stains the cell populations.

25. A method for immobilizing and detecting one or more cell populations in a sample comprising:
(a) introducing a sample, a first capture complex comprising a first encoded magnetic bead and a first antibody having a specific affinity for a first epitope on a first cell population that may be present in the sample, and a second capture complex comprising a second encoded magnetic bead and a second antibody having a specific affinity for a second epitope on the first cell population that may be present in the sample into a chamber;
(b) applying a magnetic field to the chamber to attract magnetically responsive aggregates of the first population of cells, the first capture complex and the second capture complex to a surface of the chamber; and
(c) detecting the first population of cells, the encoded magnetic beads of the first capture complex, and the encoded magnetic beads of the second capture complex that are immobilized on the surface of the chamber.

26. The method of claim 25, further comprising enumerating the first population of cells.

27. The method of claim 26, further comprising determining whether a statistically significant number of the first population of cells are immobilized on the surface of the chamber, and introducing an additional amount of the sample into the chamber until a statistically significant number of the first and second populations of the cells are immobilized on the surface of the chamber.

28. The method of claim 25, further comprising introducing into the chamber a third capture complex comprising a third encoded magnetic bead and a third antibody having a specific affinity for a third epitope on a second cell population that may be present in the sample, and detecting and enumerating the second population of cells that are immobilized in a magnetically responsive aggregate with the third capture complex on the surface of the chamber.

29. The method of claim 28, further comprising determining a ratio of the first population of cells to the second population of cells.

30. The method of claim 27, further comprising determining the concentration of the first population of cells in the sample.

31. The method of claim 28, further comprising determining the concentration of the second population of cells in the sample.

32. The method of claim 25, further comprising staining the cell population with a generic reporter dye that stains cell membranes or a generic reporter dye that stains cell nuclei.

33. The method of claim 32, wherein detecting the cell populations comprises taking a first classification image to detect a signal from the encoded magnetic beads of the first capture complex, taking a second classification image to detect a signal from the encoded magnetic beads of the second capture complex, and taking a reporter image to detect a signal from the generic reporter dye that stains the cell populations.

34. The method of claim 1, wherein the encoded magnetic bead is between 5-8 μm in diameter.

35. The method of claim 16, wherein the encoded magnetic bead is between 5-8 μm in diameter.

36. The method of claim 25, wherein the encoded magnetic bead is between 5-8 μm in diameter.

\* \* \* \* \*